(12) United States Patent
Jung et al.

(10) Patent No.: US 7,972,379 B2
(45) Date of Patent: Jul. 5, 2011

(54) AIDING APPARATUS FOR NASAL CARTILAGE STRUT IN NASAL TIP SURGERY

(75) Inventors: Young Chul Jung, Gyeoggi-do (KR); Gi Pyo Im, Gyeoggi-do (KR)

(73) Assignees: Young Chul Jung, Suwon, Gyeoggi-do (KR); Gi Pyo Im, Suwon, Gyeoggi-do (KR); Hong Kim, Cheonan, Chungnam (KR); Glotech Co., Ltd., Asan, Chungnam (KR)

( * ) Notice: Subject to any disclaimer, the term of this patent is extended or adjusted under 35 U.S.C. 154(b) by 0 days.

(21) Appl. No.: 12/664,217

(22) Filed: Dec. 11, 2009

(65) Prior Publication Data
US 2010/0185282 A1 Jul. 22, 2010

Related U.S. Application Data

(63) Continuation-in-part of application No. PCT/KR2008/001241, filed on Mar. 5, 2008.

(30) Foreign Application Priority Data

Jun. 11, 2007 (KR) .......................... 10-2007-0056576

(51) Int. Cl.
*A61F 2/18* (2006.01)

(52) U.S. Cl. .......................................................... 623/10
(58) Field of Classification Search ..................... 623/10; 606/204.45
See application file for complete search history.

(56) References Cited

U.S. PATENT DOCUMENTS

| 5,030,232 A | 7/1991 | Pham |
| 5,112,353 A | 5/1992 | Johansson et al. |
| 5,736,372 A | 4/1998 | Vacanti et al. |
| 6,454,803 B1 | 9/2002 | Romo, III |

OTHER PUBLICATIONS

International Search Report from PCT/KR2008/001241, Mailed Jun. 16, 2008.

*Primary Examiner* — Suzette J Gherbi
(74) *Attorney, Agent, or Firm* — Edwards Angell Palmer & Dodge LLP; Kongsik Kim

(57) ABSTRACT

An aiding apparatus for nasal tip plasty is useable in augmentation rhinoplasty. The aiding apparatus for nasal tip plasty includes a strut part and a holding part provided on a lower portion of the strut part and coupled to septal cartilage. Thus, a cartilage scaffold complex useable in nasal tip plasty may be easily prepared at the exterior of an operation space. This aiding apparatus allows substitution for the paired batten graft or paired spreader graft and easier execution of caudal septal extension graft. Further, a decreased amount of cartilage is used to execute the nasal tip plasty in a simple way, therefore easily making a pretty nose, in addition to shortening the operation time.

15 Claims, 26 Drawing Sheets

AIDING APPARATUS FOR NASAL CARTILAGE STRUT IN NASAL TIP SURGERY

CROSS-REFERENCE TO RELATED APPLICATIONS

This is a continuation-in-part application of PCT/KR2008/001241 filed on Mar. 5, 2008, which claims the benefit of Korean Application No. 10-2007-0056576 filed on Jun. 11, 2009, the entire contents of which are incorporated herein by reference.

TECHNICAL FIELD

The present invention relates, in general, to an aiding apparatus for nasal tip plasty, which is performed to elevate the nose and, more particularly, to an aiding apparatus for nasal tip plasty, which allows easy fabrication of a cartilage scaffold complex used in nasal tip plasty outside an operation space, substitutes for the paired batten graft or the paired spreader graft, and allows easy operation of the caudal septal extension graft.

BACKGROUND ART

As alloplastic materials used in nasal tip plasty, medical silicone (dimethylsiloxane polymer) which is widely known to those skilled in the art, is mainly used. Further, Gore-Tex, polyethylene terephthalate, Proplast I and II (Medpore™), etc. are used as the alloplastic materials. Meanwhile, as natural materials, autologous cartilage is used in augmentation rhinoplasty.

Such alloplastic materials are of limited use when highly elevating a nasal tip.

It is because the elevation of a nasal tip using alloplastic materials (mainly silicone implants) interferes with the blood supply to the tip of the nose, thus causing the nasal tip to become red. Further, it has been reported that the alloplastic materials frequently penetrate the nasal tip.

For these reasons, when a nasal tip must be very highly elevated, autologous cartilage is commonly used.

Since autologous cartilage can make a much more beautiful nasal tip in the augmentation rhinoplasty, in comparison with silicone, plastic surgeons prefer autologous cartilage to silicone in the nasal tip plasty.

In the case of using autologous cartilage, ear cartilage or septal cartilage is mainly used, as shown in FIGS. 15 and 17. However, an operation using the autologous cartilage has a drawback in that more effort and time are required, compared to an operation using a silicone implant.

Nasal tip plasty using autologous cartilage is performed as follows.

Generally, a silicone implant or Gore-Tex is used for the dorsum (or, ridge) of the nose. Nasal tip plasty using autologous cartilage is performed on a nasal tip.

When the nose being subjected to augmentation rhinoplasty is cut open, as shown in FIG. 16, the nasal ridge (nasal vault) is divided into a cartilaginous vault and a bony vault.

As shown in FIGS. 16 and 17, the cartilaginous vault includes upper lateral cartilage and septal cartilage.

When viewing the upper lateral cartilage from the front, the upper lateral cartilage has a triangular shape and is firmly coupled to a nasal bone. This becomes the foundation of the nose, and includes the upper lateral cartilage, the nasal bone, the septal cartilage, and a perpendicular plate of the ethmoid bone.

Meanwhile, as shown in FIGS. 18 and 19, the lower lateral cartilage is divided into medial crura, middle crura, and lateral crura. A tip defining point (TDP) is defined by the vaults of the middle crura, a supratip breakpoint, and an infratip breakpoint. When viewing the lower lateral cartilage from the front, the lower lateral cartilage is seen to have a diamond shape (see FIG. 20).

The nasal tip includes the lower lateral cartilage. The shape of the nasal tip is mainly determined by the shape and structure of the lower lateral cartilage (see FIG. 19).

The work of harvesting the cartilage is conducted by harvesting some ear cartilage or septal cartilage, as shown in FIGS. 15 and 17.

When nasal tip plasty is performed after the cartilage is harvested, the cartilage is divided into several pieces, according to the intended purpose.

First, as shown in FIGS. 21 to 23, a strut is made of the cartilage and then is set up on the columellar.

When the medial crura of the lower lateral cartilage are secured to the strut, tension sufficient to elevate the nasal tip is created. In this state, cap grafting (see FIG. 23) or shield grafting (see FIG. 22) is performed, thus forming the nose into an intended shape.

When the strut is set up the strut is frequently connected to an upper border of the septal cartilage or the anterior nasal spine (see FIG. 21). The upper border is a region of a nose defined from the dorsum to the anterior nasal spine. Especially when the strut is held on the upper border of the septal cartilage, the parts must be stitched to each other one by one in a narrow space, which takes a long time.

Further, this method is problematic in that the cartilage is apt to warp or be deformed, so that it is difficult to make an intended shape. To solve this problem, there is used the paired batten graft for doubly placing cartilage to the septal cartilage in a columellar direction or the paired spreader graft for doubly placing cartilage to the septal cartilage in a cephalocaudal direction. However, this method consumes more cartilage and increases time taken for operation.

The above information disclosed in this Background section is only for enhancement of understanding of the background of the invention and therefore it may contain information that does not form the prior art that is already known in this country to a person of ordinary skill in the art.

SUMMARY OF DISCLOSURE

Accordingly, the present invention has been made keeping in mind the above problems occurring in the prior art, and an object of the present invention is to provide an aiding apparatus for nasal tip plasty, in which a structure such as frame and scaffold using a non-toxic material is provided, and a cartilage scaffold complex used in cap grafting or shield grafting is manufactured from the exterior with minimal use of cartilage, so that the cartilage scaffold complex can be easily held on the upper border of the septal cartilage in a narrow surgical view, and thus a nasal tip having an intended shape can be obtained within a short period of time.

Another object of the present invention is to provide various methods, in which a scaffold serving as a support and providing a standard frame is made of biodegradable plastics, autologous cartilage is placed in the scaffold, and then the scaffold is biodegraded to disappear, thus minimizing the sensation of foreign body.

Still another object of the present invention is to provide an aiding apparatus for nasal tip plasty, which may substitute for the paired batten graft or the paired spreader graft and allow easy operation of caudal septal extension graft.

In order to accomplish the above objects, the present invention provides an aiding apparatus for nasal tip plasty, which includes a strut part; and a holding part provided on a lower portion of the strut part and coupled to septal cartilage.

Preferably, the holding part is coupled to an upper border of the septal cartilage. As an example, the holding part is secured to an upper border of the septal cartilage in a columellar direction. As another example, the holding part is secured to an upper border of the septal cartilage in a cephalo-caudal direction. Selectively, a seating part may be formed in the strut part, and an extension graft cartilage may be secured to the seating part.

In one aspect of the present invention, a ceiling part may be formed a top of the strut part such that cartilage for cap grafting is held thereon.

In another aspect of the present invention, a seating part may be formed on the strut part such that cartilage strut is seated therein. In this case, a sensation of foreign body may be decreased.

Preferably, the holding part may have a leg part which is coupled to the septal cartilage. Selectively, the leg part may have serrated parts on inner surfaces at both sides thereof. The serrated parts play a role of securing the leg part to the septal cartilage by engagement without stitching, thereby increasing the easiness of nasal tip plasty within a narrow operation space.

In still another aspect of the present invention, the strut part and the holding part may include a first unit and a second unit, which are separative from each other, and a coupling part for coupling the first unit and the second unit with each other. In this case, a seating part is preferably formed at an upper side of the coupling part such that cartilage strut is inserted therein, and a leg part is preferably formed at a lower side of the coupling part such that the leg part is secured to the septal cartilage.

Preferably, stitching holes are formed in the strut part, the holding part and a ceiling part.

If the aiding apparatus for nasal tip plasty according to the present invention is used for nasal tip plasty, a cartilage scaffold complex allowing cap graft or shield graft may be prepared at the outside with a minimal amount of cartilage and then easily secured to an upper border of septal cartilage within a narrow operation visual field, so nasal tip plasty may be executed within a very short time into an intended shape. Also, the present invention may substitute for the paired batten graft or paired spreader graft using autologous cartilage and also facilitate caudal septal extension graft.

BRIEF DESCRIPTION OF DRAWINGS

Other objects and aspects of the present invention will become apparent from the following description of embodiments with reference to the accompanying drawing in which.

Figure 1:
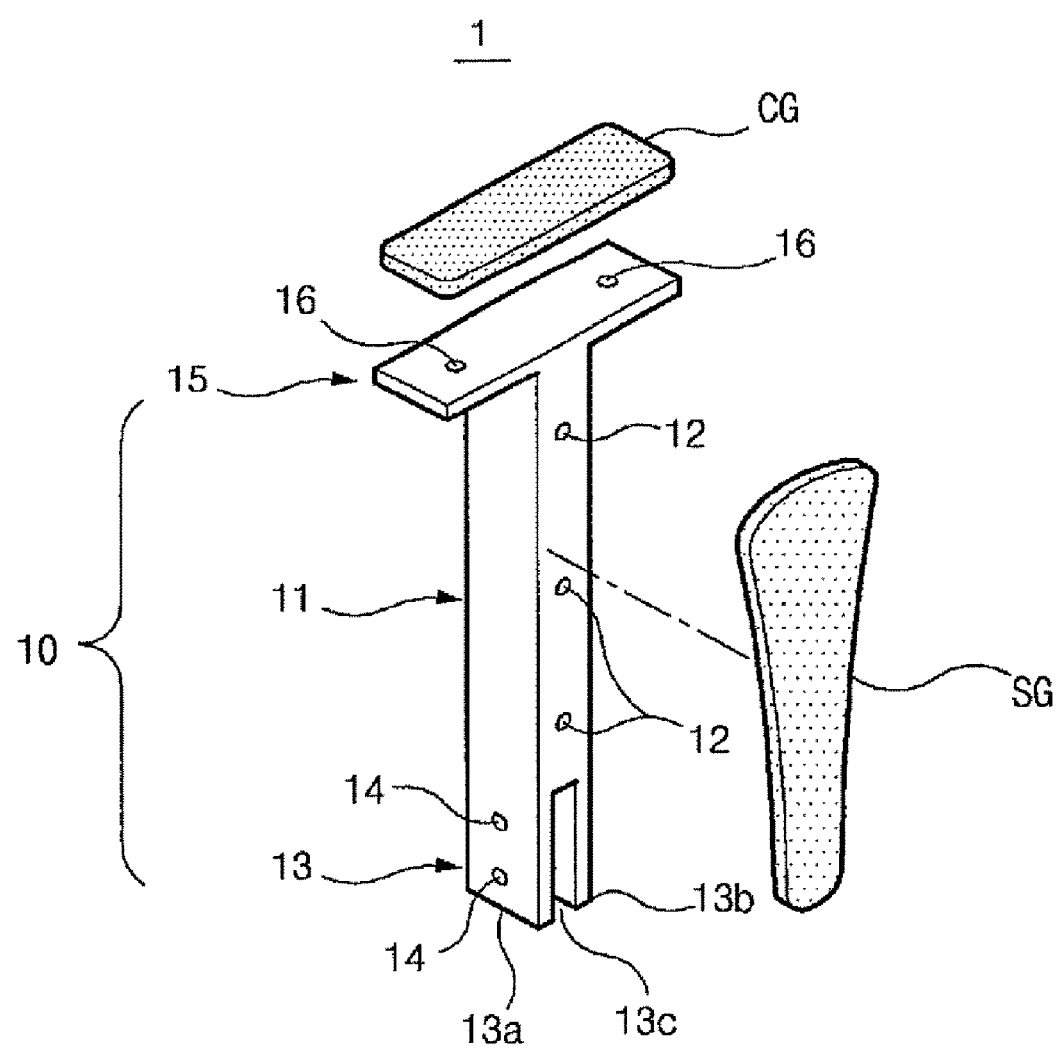
FIG. 1 is an exploded perspective view showing a first cartilage scaffold complex using a first aiding apparatus for nasal tip plasty, according to the first embodiment of the present invention.

DESCRIPTION OF REFERENCE CHARACTERS OF IMPORTANT PARTS 1,3,5: cartilage scaffold complex
10,30,50,70: aiding apparatus
11,31,51,71a,71b: strut part
13,33,53,73: holding part
13a, 13b;33a,33b;53a,53b;73a,73b: leg part
13c,33c,53c,73c: support groove
15,35,55,75a,75b: ceiling part
34a,34b: serrated part
51a,71c: seating part
77a,77b: coupling part
78: base part
CG: cap graft cartilage
SG: shield graft cartilage
SC: septal cartilage
ST: cartilage strut

DETAILED DESCRIPTION OF DISCLOSURE

Hereinafter, preferred embodiments of the present invention will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just a preferable example for the purpose of illustrations only, not intended to limit the scope of the invention, so it should be understood that other equivalents and modifications could be made thereto without departing from the spirit and scope of the invention.

First Embodiment

Figure 2:
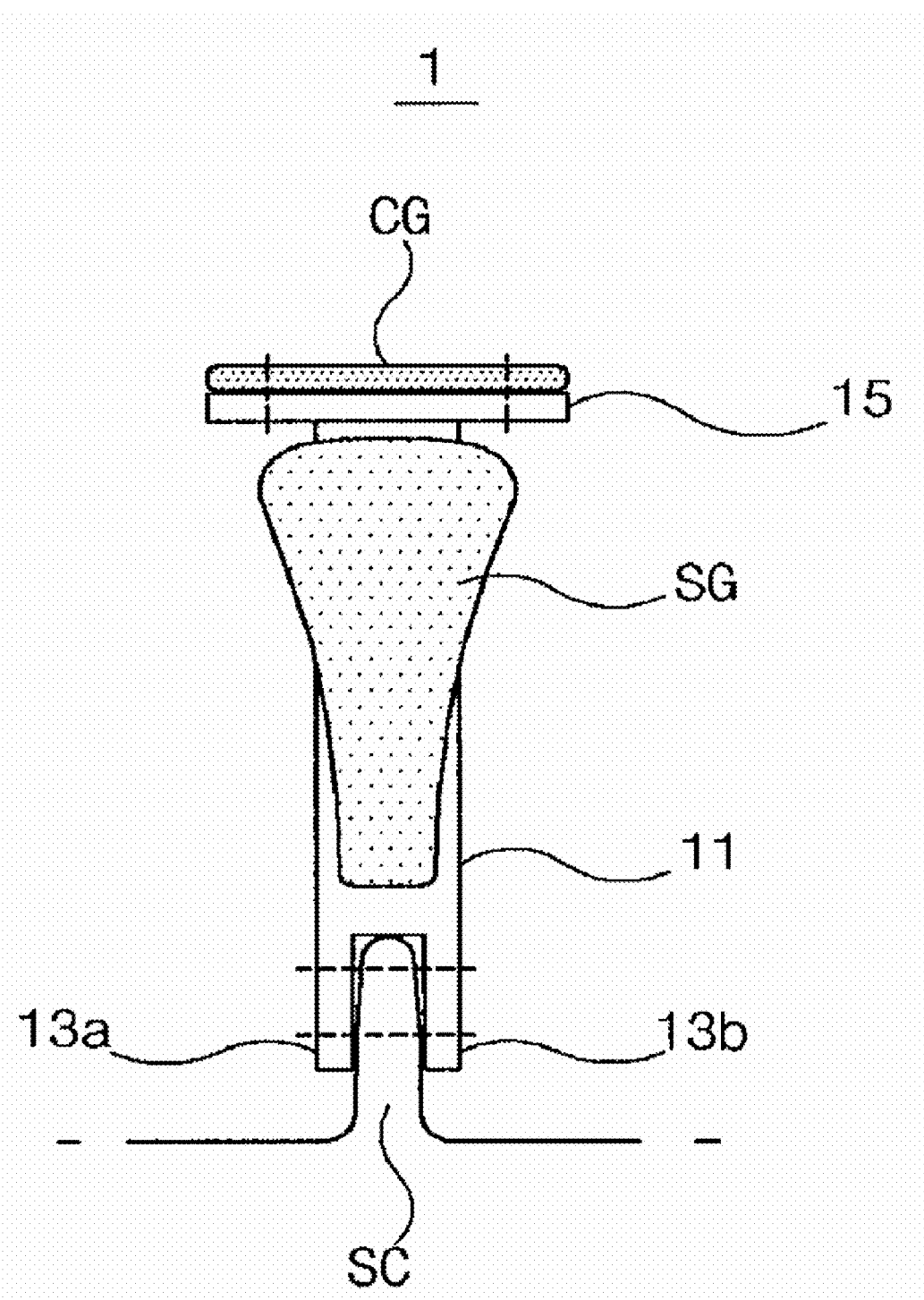
FIG. 2 is a view showing the state in which the first cartilage scaffold complex is secured to the upper border of septal cartilage.

FIG. 1 is an exploded perspective view showing the first cartilage scaffold complex 1 using the first aiding apparatus for nasal tip plasty, according to the first embodiment of the present invention, and FIG. 2 is a view showing the state in which the first cartilage scaffold complex 1 is secured to the upper border of septal cartilage.

As shown in FIGS. 1 and 2, the aiding apparatus 10 for nasal tip plasty according to the first embodiment of the present invention includes a strut part 11 and a holding part 13.

Based on clinical tests, a material which is capable of minimizing known medical side effects, including interference with the blood supply to a nasal tip or allergies, is selected for the aiding apparatus 10.

Preferably, the selected material is a non-toxic and biocompatible non-absorbable polymer or a non-toxic and biocompatible biodegradable polymer.

The strut part 11 serves as a columellar support for the elevation of the nasal tip.

Further, the strut part 11 functions as a support part for shield graft cartilage SG.

The shield graft cartilage SG is commonly used in the elevation of the nasal tip. At this time, the shield graft cartilage SG is the important part that determines the final shape of the nasal tip. To make the shield graft cartilage, the nasal septal cartilage is the most preferred material. However, other cartilages may be used to make the shield. A cartilage harvested and carved to have the shape of a shield so that both sides of the cartilage define the tip defining point (TDP). Preferably, the upper portion of the shield graft cartilage SG has a width from about 6 to 8 mm.

Stitching holes 12 are formed in the strut part 11 so as to fasten the shield graft cartilage SG to the strut part. Thus, the shield graft cartilage SG is fastened to the strut part 11 using a stitching suture.

As an alternative, a biodegradable pushpin may be used in place of the stitching suture to fix the shield graft cartilage SG. In the following explanation, all cartilages are fixed using switching sutures or biodegradable pushpins without any special mention.

The holding part 13 includes leg parts 13a and 13b, with a support groove 13c defined between the leg parts.

Such a construction allows the support groove 13c between the leg parts 13a and 13b to be easily inserted into the upper border of the nasal septal cartilage SC, thus allowing an operation to be performed within a short period of time.

Stitching holes 14 are formed in the leg parts 13a and 13b, similarly to the strut part 11. Thus, the nasal septal cartilage SC can be firmly fastened to the leg parts 31a, 31b using stitching sutures (shown by the dotted lines) to firmly fix the cartilage scaffold complex 1 to the septal cartilage SC.

The cartilage scaffold complex means a combination of a grafting cartilage and the aiding apparatus for nasal tip plasty, as disclosed in this embodiment and following embodiments. The grafting cartilage is obtained by carving autologous cartilage, harvested from a human body, as desired. The grafting cartilage includes struts, shield grafts, cap grafts, onlay cap grafts and extension grafts.

A ceiling part 15 is provided on the top of the strut part 11.

Cap graft cartilage CG for cap grafting is placed on the ceiling part 15.

The cap graft cartilage CG is the part that determines a final shape of the nasal tip. For using the cap graft cartilage CG, the nasal septal cartilage or ear cartilage is carved into several sheets with a width from about 6 to 8 mm to express the tip define point (TDP), and then the several sheets of carved cartilage are stacked to obtain a desired height. When the nasal septal cartilage or ear cartilage is stacked several times, it is required that the cartilage be firmly supported by a strong prop. The strut part 11 according to the first embodiment of this invention can more firmly support the cap graft cartilage CG with many folds, compared to the autologous cartilage.

Stitching holes 16 are formed in the ceiling part 15, thus securely supporting the cap graft cartilage CG through stitching. Of course, when stitching and securing the cap graft cartilage, a pushpin may be used in place of stitching suture.

The ceiling part 15 is connected to the middle crura of lower lateral cartilage through the stitching holes 16 by using stitching sutures.

In order to meet the convenience of manufacture or to facilitate height adjustment, the upper end of the strut part 11 may substitute for the ceiling part 15. In other words, the ceiling part 15 may not be formed at the upper portion of the strut part 11 as in the following embodiment.

As such, the shield graft cartilage SG and the cap graft cartilage CG are fastened to the strut part 11 and the ceiling part 15 of the cartilage scaffold complex 1 from the exterior. In this state, the cartilage scaffold complex is easily secured to the upper border of the septal cartilage SC. Therefore, it is not necessary to set up a strut using cartilage within a narrow surgical view, so that the time spent on an operation is reduced. Further, the amount of cartilage to be used is considerably reduced, thus alleviating a patient's pain, and allowing the patient to rapidly recover, in addition to more easily making a nose beautifully.

According to the condition of the elevation of the nasal tip, both the cap graft cartilage CG and the shield graft cartilage SG may be fastened to the cartilage scaffold complex. Either the cap graft cartilage or the shield graft cartilage may be fastened to the cartilage scaffold complex. In the case of fastening only the shield graft cartilage SG, the aiding apparatus 10 needs no ceiling part 15.

Second Embodiment

Figure 3:
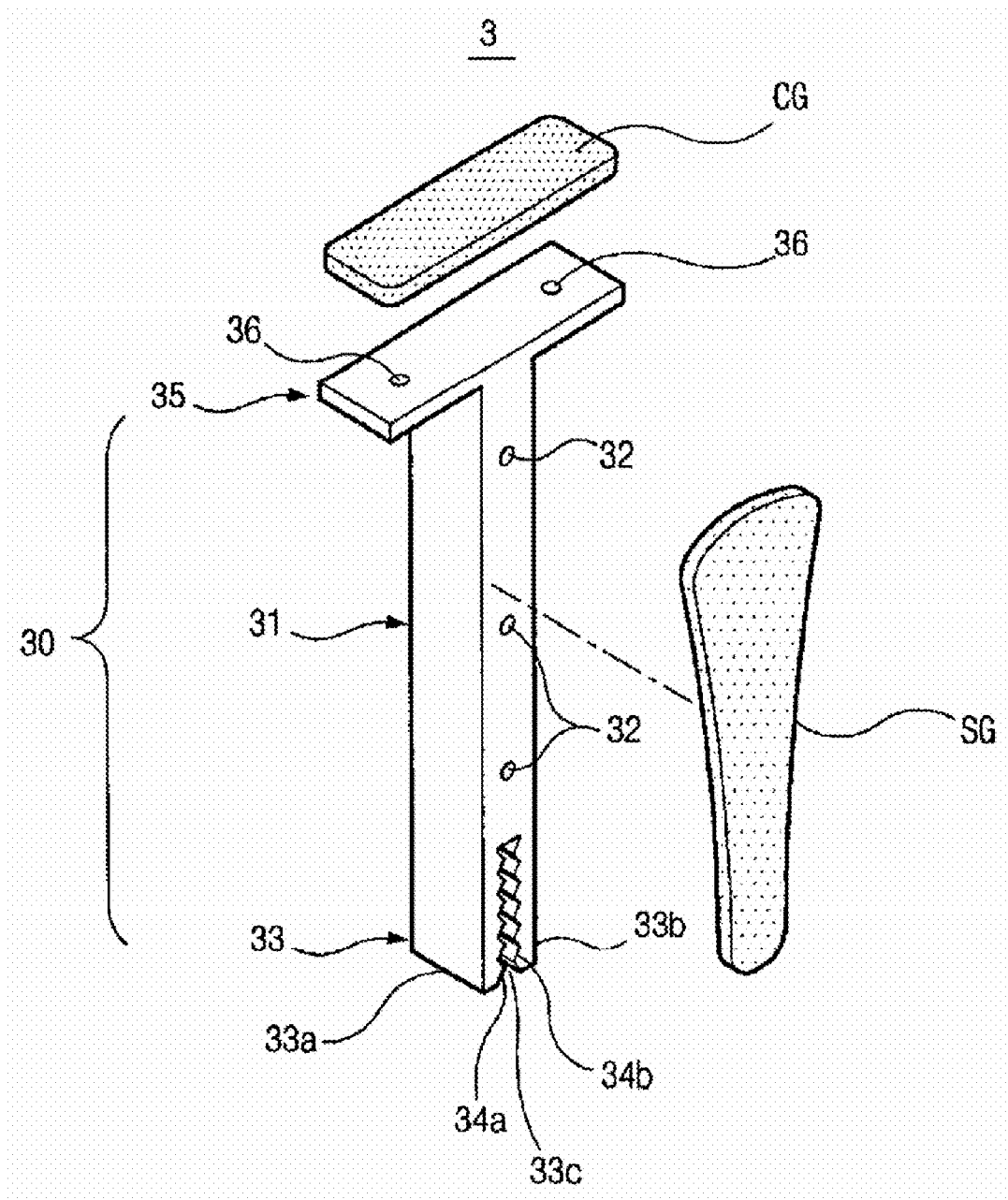
FIG. 3 is an exploded perspective view showing a second cartilage scaffold complex using a second aiding apparatus for nasal tip plasty, according to the second embodiment of the present invention.
Figure 4:
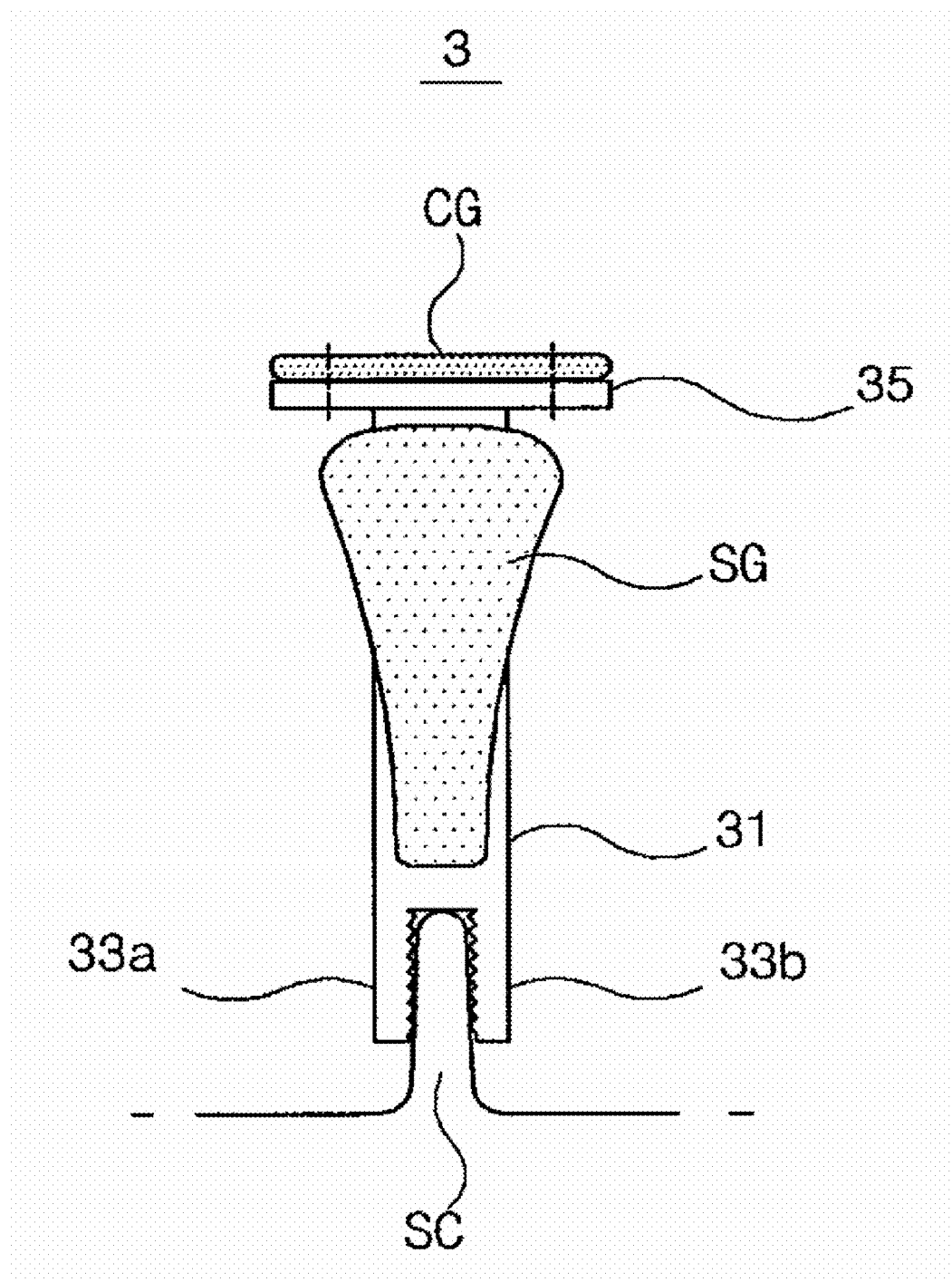
FIG. 4 is a view showing the state in which the second cartilage scaffold complex is secured to the upper border of septal cartilage.

FIG. 3 is an exploded perspective view showing the second cartilage scaffold complex 3 using the second aiding apparatus for nasal tip plasty, according to the second embodiment of the present invention, and FIG. 4 is a view showing the state in which the second cartilage scaffold complex 3 is secured to the upper border of septal cartilage.

As shown in FIGS. 3 and 4, the aiding apparatus 30 according to the second embodiment is similar in construction and function to the aiding apparatus 10 according to the first embodiment. However, unlike the first embodiment, serrated parts 34a and 34b are formed on the inner surfaces of leg parts 33a and 33b.

That is, the serrated parts 34a and 34b engage with each other, so that septal cartilage SC is held between the serrated parts. Thus, the cartilage scaffold complex 3 can be rapidly held to the upper border of the septal cartilage in a narrow operation space without the stitching operation.

Further, the aiding apparatus 30 includes stitching holes 32 which are formed in a strut part 31, and stitching holes 36 which are formed in a ceiling part 35. Thus, the cap graft cartilage CG or the shield graft cartilage SG may be stitched or connected by passing a stitching suture through the stitching holes or inserting push pins into the stitching holes. Thereby, a cartilage scaffold complex 3 is achieved.

Third Embodiment

Figure 5:
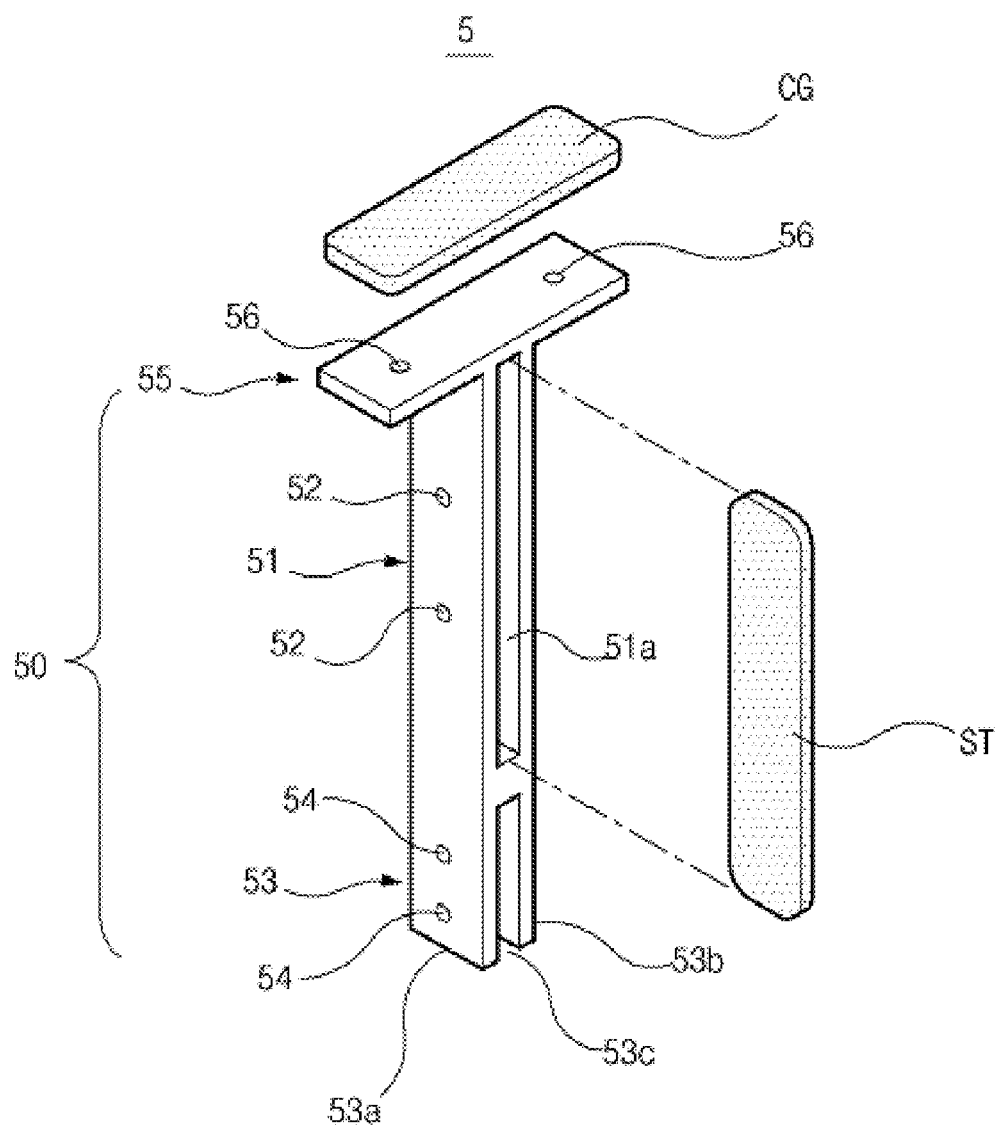
FIG. 5 is an exploded perspective view showing a third cartilage scaffold complex using a third aiding apparatus for nasal tip plasty, according to the third embodiment of the present invention.
Figure 6:
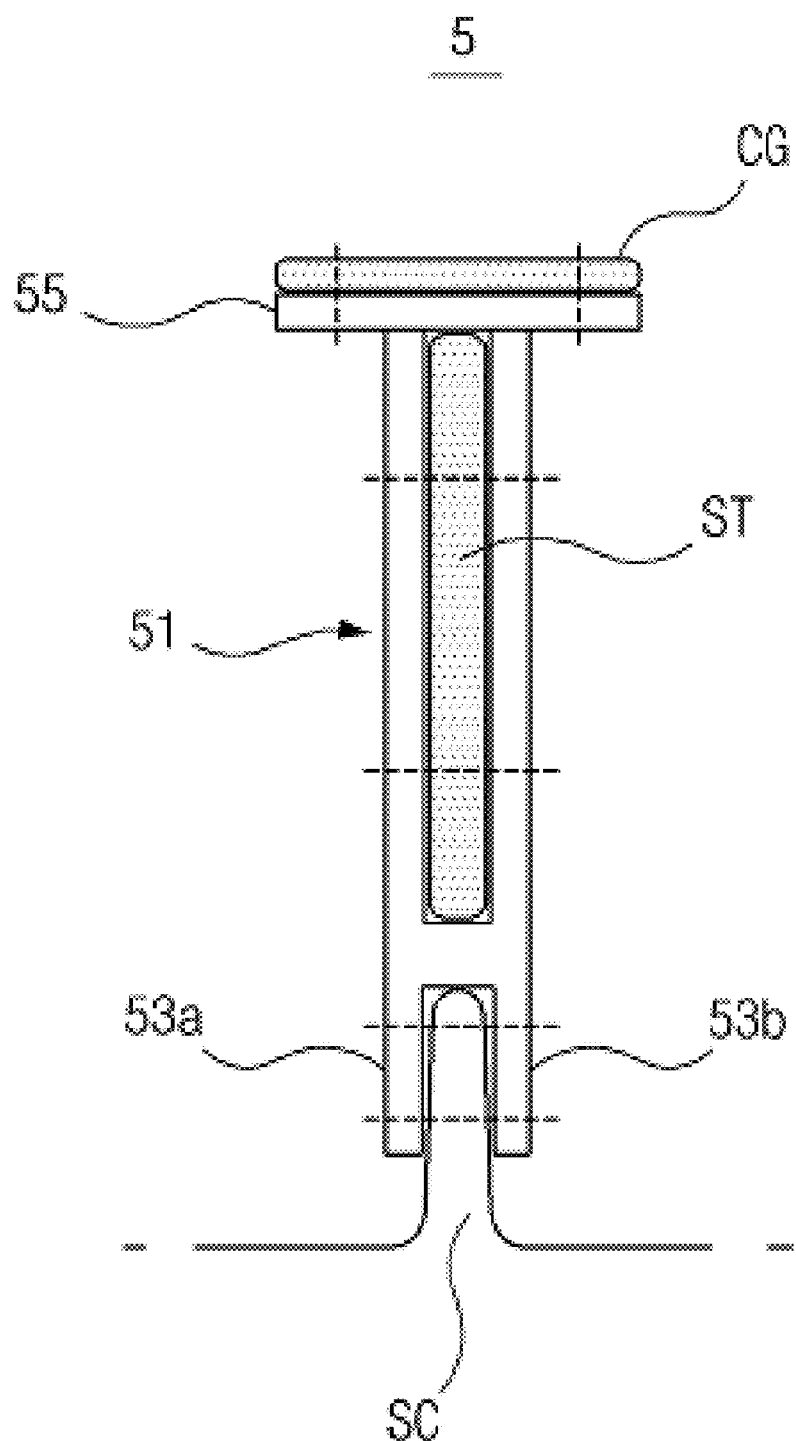
FIG. 6 is a view showing the state in which the third cartilage scaffold complex is secured to the upper border of septal cartilage.

FIG. 5 is an exploded perspective view showing the third cartilage scaffold complex 5 using the third aiding apparatus for nasal tip plasty, according to the third embodiment of the present invention, and FIG. 6 is a view showing the state in which the third cartilage scaffold complex 5 is secured to the upper border of septal cartilage.

As shown in FIGS. 5 and 6, the aiding apparatus 50 of the third embodiment is different from the aiding apparatuses of the first and second embodiments in that a seating part 51a is provided in a strut part 51 so that a cartilage strut ST is seated in the seating part, and the aiding apparatus 50 is made of a biodegradable polymer material.

In detail, the aiding apparatus 50 serves as a scaffold which is decomposed and disappears after a predetermined period of time has passed.

One coupling hole 52 or a plurality of coupling holes 52 is formed in the seating part 51a so as to support the cartilage strut ST which is seated in the seating part. The cartilage strut ST is fastened to the seating part 51a using a stitching suture.

While the cartilage strut ST is supported and grows in the seating part 51a, the cartilage strut forms an intended shape within a few months. At this time, the aiding apparatus 50 is decomposed and disappears. Thus, it is possible to minimize the sensation of foreign body, and achieve a more natural cartilage structure.

Further, stitching holes 52, 54, and 56 are formed in the aiding apparatus 50, so it is possible to secure the cap graft cartilage CG to the ceiling part 35 or secure a leg part 53 to the upper border of the septal cartilage by passing a stitching suture through the stitching holes or inserting push pins into the stitching holes.

Various medical instruments using biodegradable polymer materials have been used in a medical field. The biodegradable polymer materials include absorbable stitching sutures, osteocement for curing fractures, biological glue, a drug delivery system (DDS), and others. As bone conjugation plates or screws, StarScrew (Bionix, Inc.), BioScrew (Linvatec, Inc.), etc. have been developed. Recently, plastic surgeons have used an auxiliary material (Endotine™ Coapt systems, Inc.) for facelifts and browlifts.

In order to implant a biodegradable polymer material into the body, the material must have biodegradability and biocompatibility. Further, the material must be sterilizable, in addition to being easily manipulable. Furthermore, degradation products must not be toxic. Moreover, the biodegradable polymer material must decompose at a proper speed according to the intended purpose, and must maintain proper mechanical strength.

Since many biodegradable polymer materials satisfy the above-mentioned requirements, they are used as a medical material. Among the biodegradable polymer materials, polylactic acid (PLLA), polyglycolic acid (PGA), polylactic acid-co-glycolic acid (PLGA copolymer), polyhydroxyalkanoate (PHA), polyhydroxybutyrate (PHB), and polycaprolactone (PCL) have proper mechanical strength, biocompatibility, biodegradability, and processability. For these reasons, the above-mentioned materials may be used as preferred biodegradable polymer materials of the present invention.

Generally, medical material using PGA loses mechanical strength after 4 to 8 weeks have passed. It takes 3 to 6 months to decompose PLLA. Thus, a proper material must be selected in consideration of the decomposition period.

Fourth Embodiment

Figure 7:
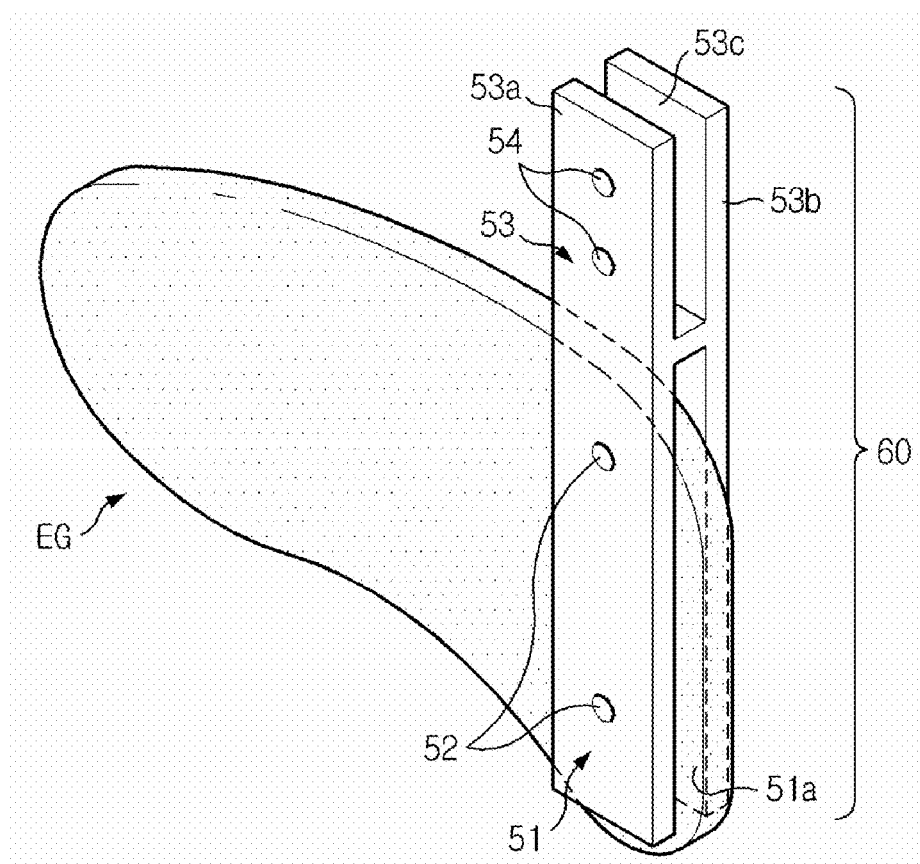
FIG. 7 is a perspective view showing a fourth aiding apparatus for nasal tip plasty to which an extension graft is fixed, according to the fourth embodiment of the present invention.

FIG. 7 is a perspective view showing the fourth aiding apparatus for nasal tip plasty according to the fourth embodiment of the present invention.

The aiding apparatus 60 according to the fourth embodiment allows substituting for the paired batten graft or the paired spreader graft using autologous cartilage at the nasal tip plasty. The aiding apparatus 60 of the fourth embodiment is substantially identical to that of the third embodiment, except that no ceiling part is provided thereto. In FIG. 7, the aiding apparatus 60 is illustrated such that the leg part 53 is located at an upper portion, and the strut part 51 is located at a lower portion.

Figure 13:
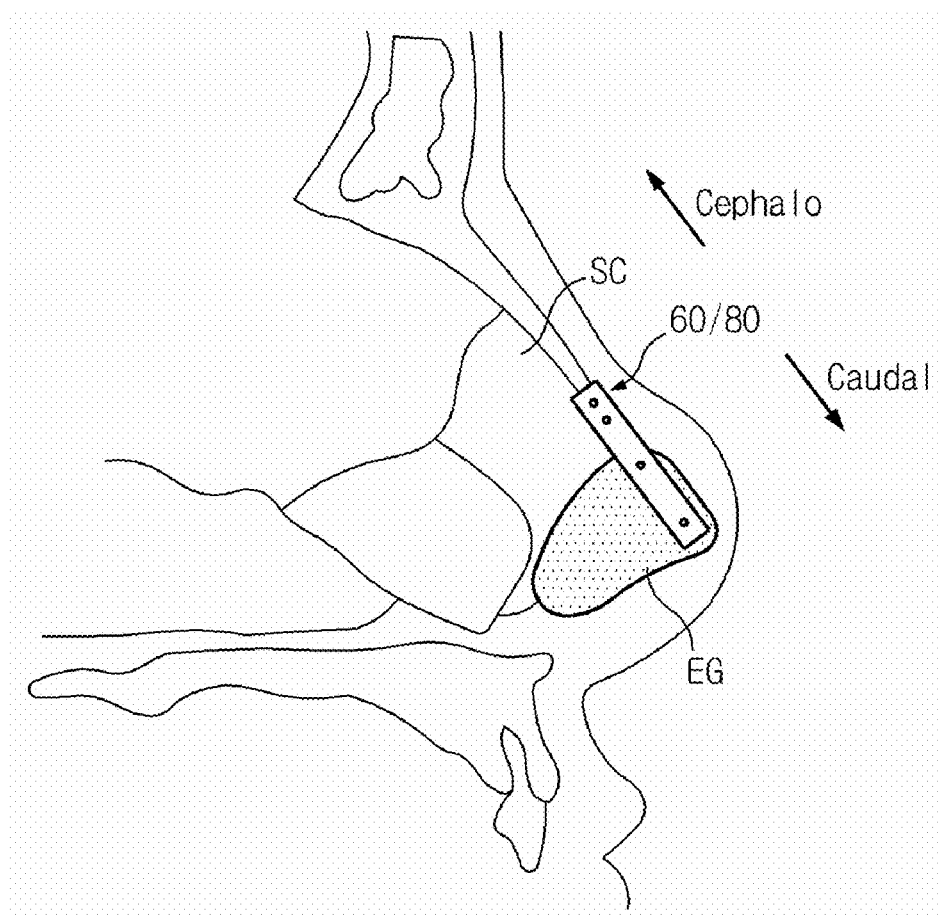
FIG. 13 is a view showing that the aiding apparatus for nasal tip plasty according to the embodiment of the present invention is fixed to the upper border of septal cartilage in a cephalo-caudal direction, and an extension graft is fixed to the aiding apparatus.

The aiding apparatus 60 may be secured to the septal cartilage SC as shown in FIG. 13. In other words, a support groove 53c formed in the leg part 53 of the aiding apparatus 60 is inserted into the upper border of the septal cartilage SC in a cephalo-caudal direction, and the leg part 53 is secured to the septal cartilage using stitching sutures or push pins. In this way, the paired spreader graft using autologous cartilage may be substituted.

Also, as required, the extension graft cartilage EG may be secured to the seating part 51a provided at the strut part 51 by using stitching sutures or push pins, which may substitute for the caudal septal extension graft.

Figure 8:
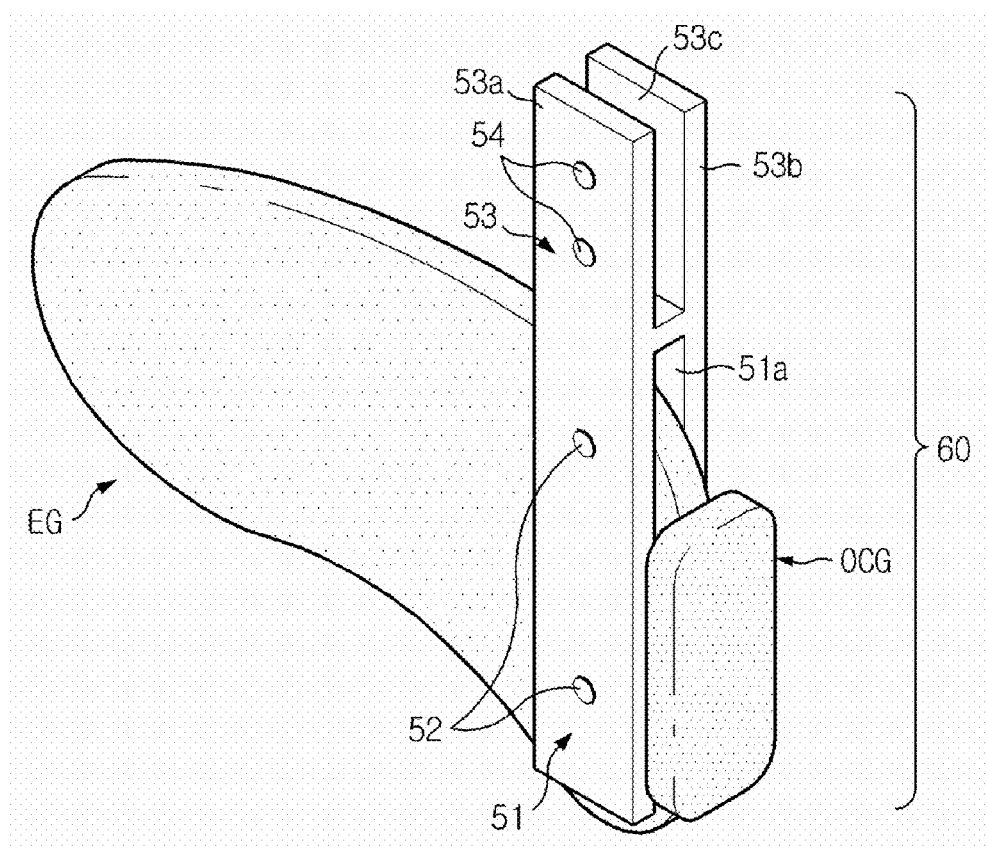
FIG. 8 is a perspective view showing the fourth aiding apparatus to which an extension graft is fixed, an onlay cap graft being further fixed to an upper portion of the extension graft, according to the fourth embodiment of the present invention.
Figure 14:
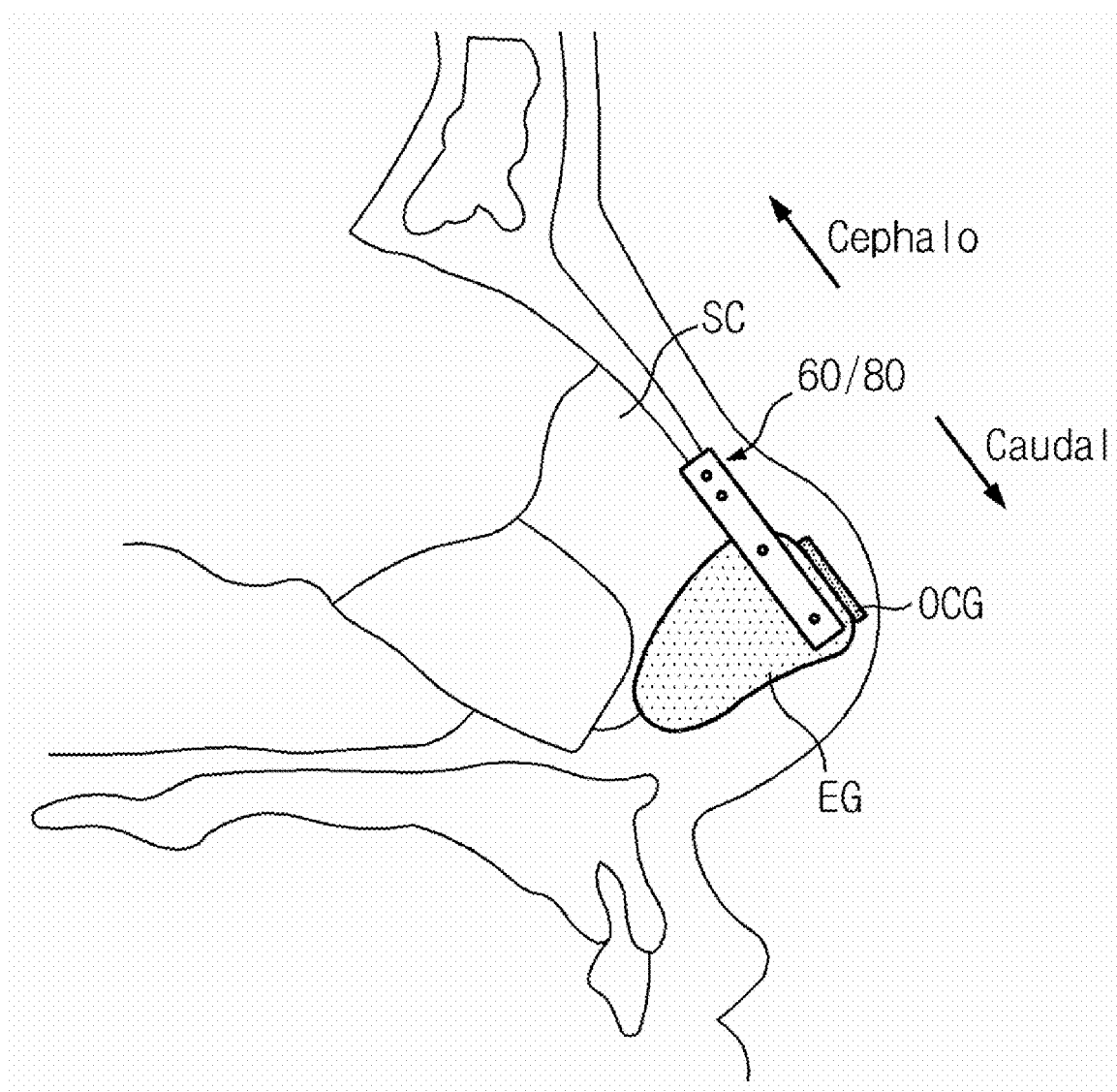
FIG. 14 is a view showing that the aiding apparatus for nasal tip plasty according to the embodiment of the present invention is fixed to the upper border of septal cartilage in a cephalo-caudal direction, an extension graft is fixed to the aiding apparatus, and then an onlay cap graft is fixed onto the extension graft.
Figure 15:
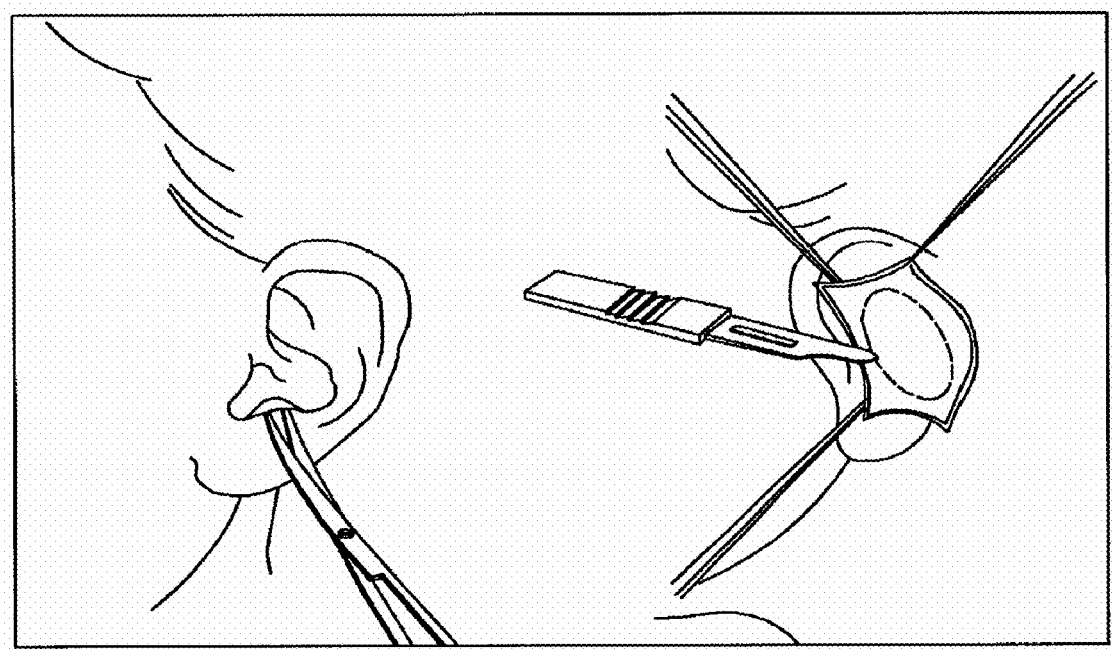
FIGS. 15 to 23 are schematic views showing the anatomical chart of the nose and nasal tip plasty.
Figure 16:
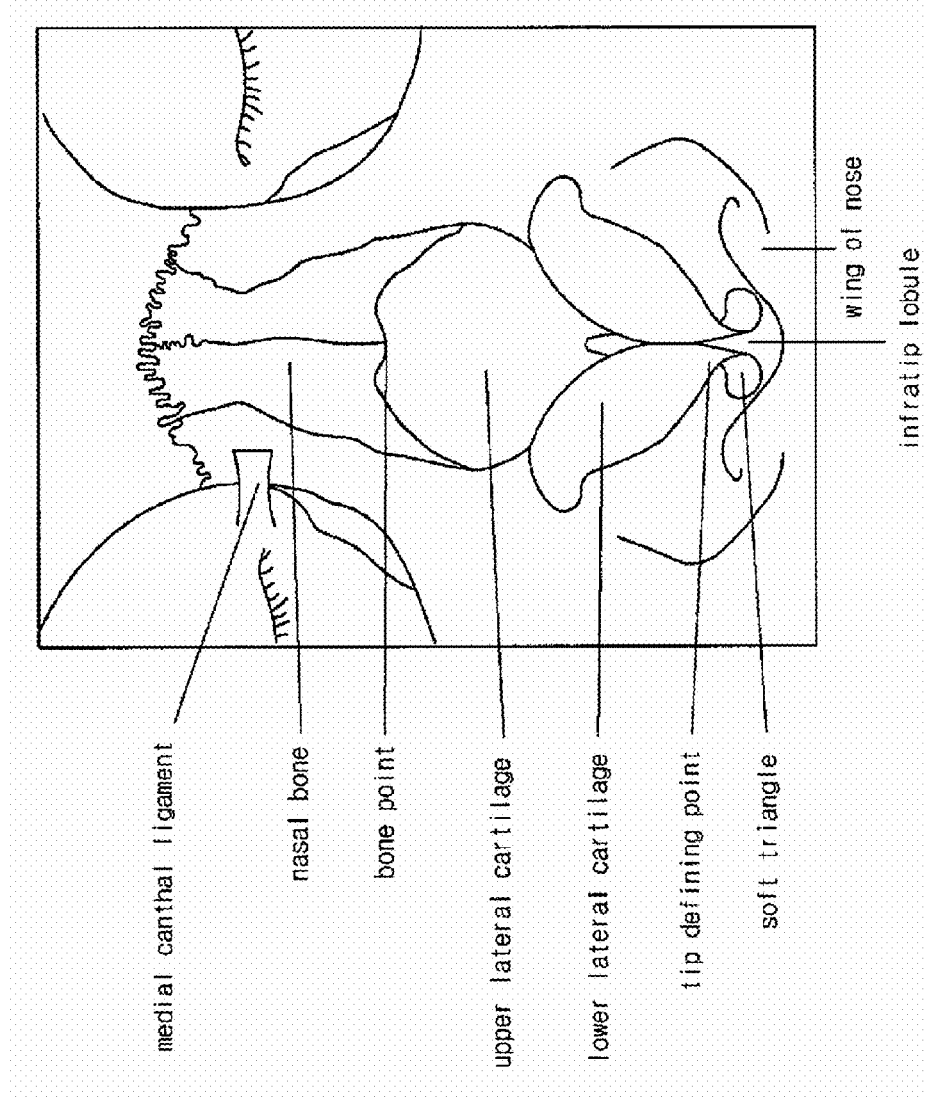
Figure 17:
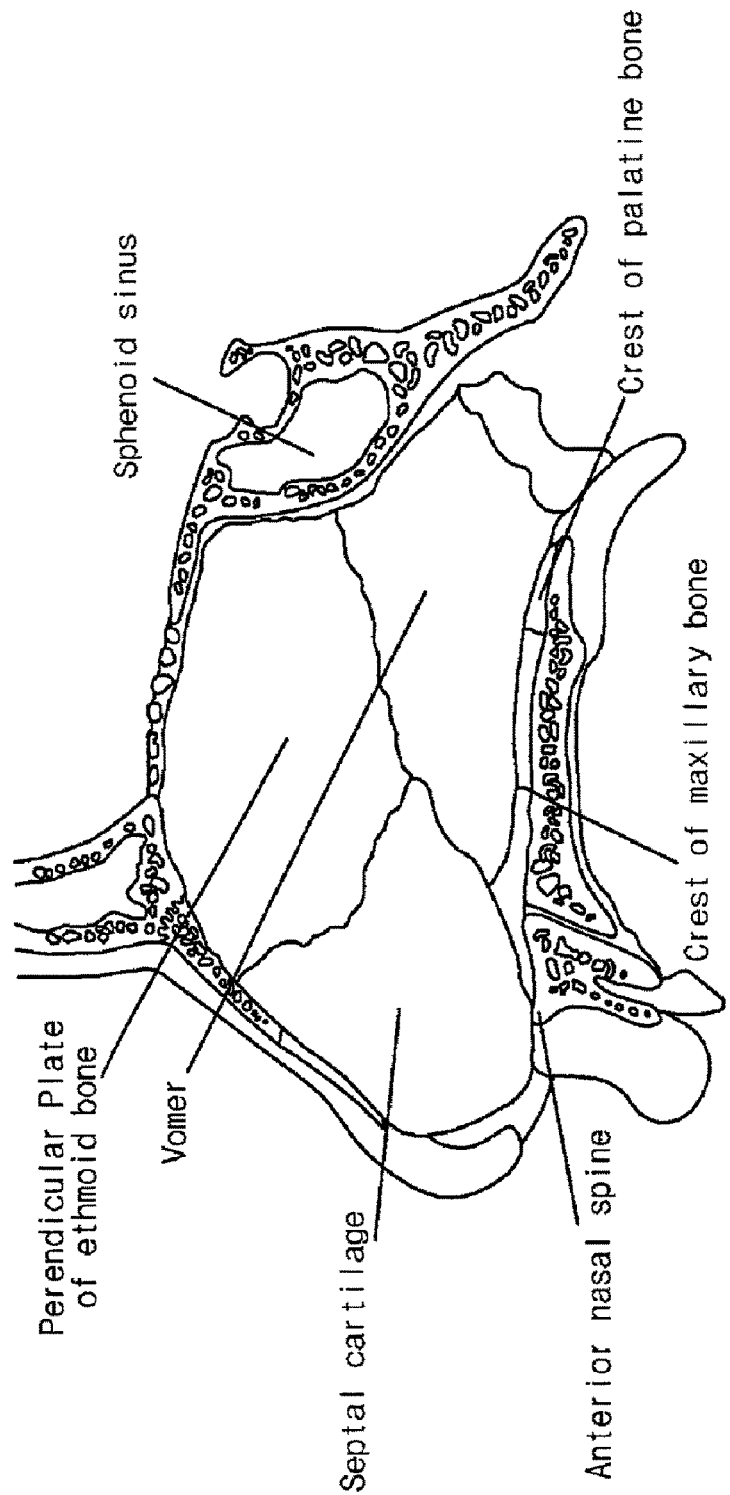
Figure 18:
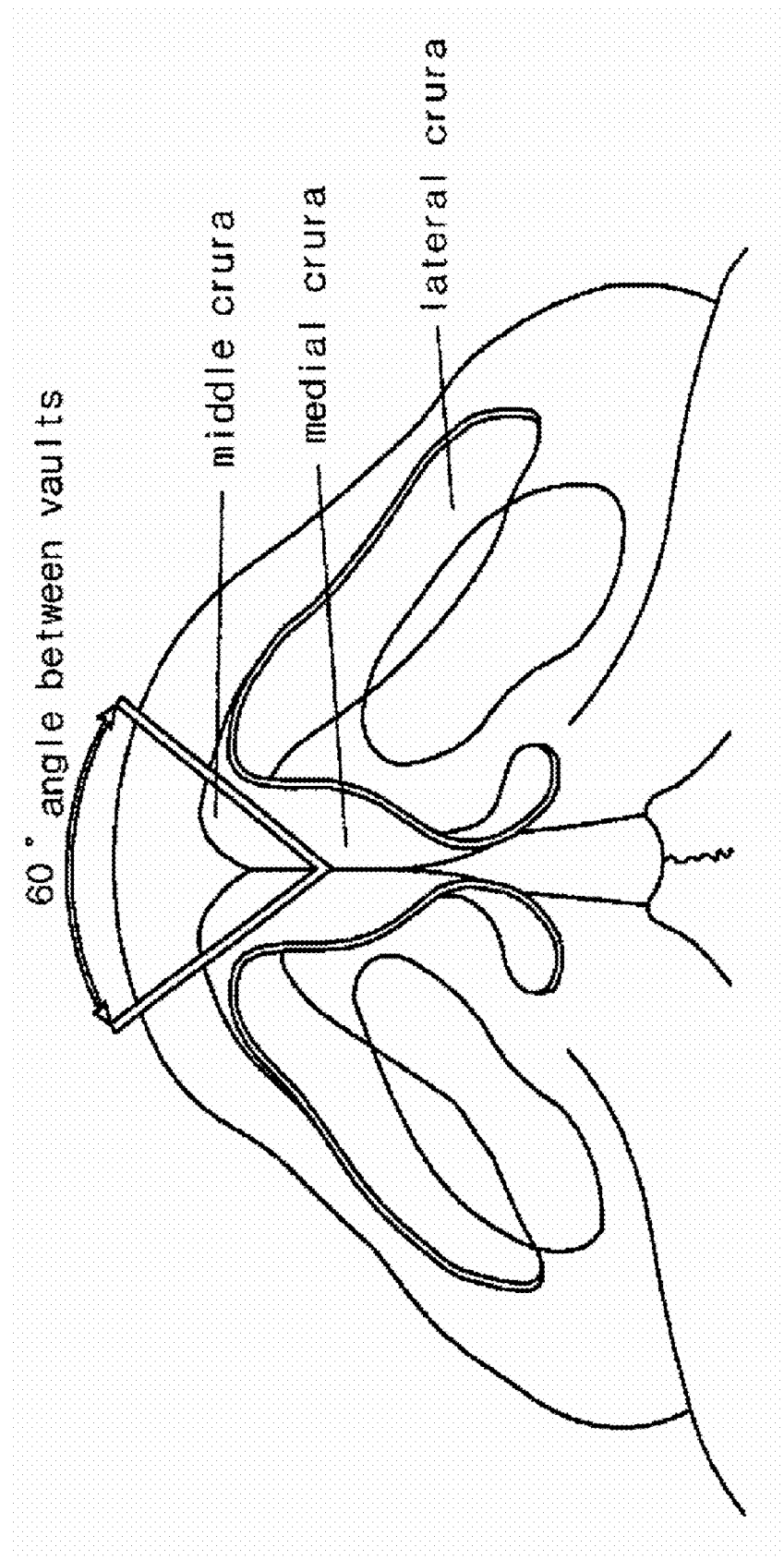
Figure 19:
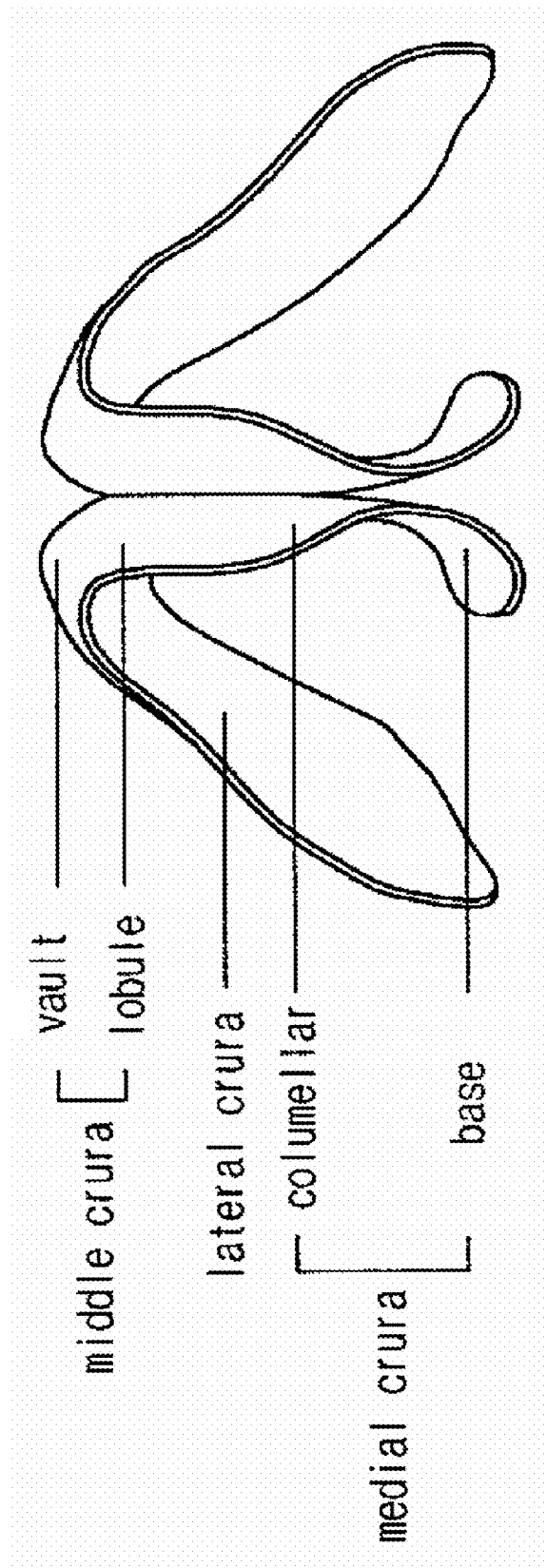
Figure 20:
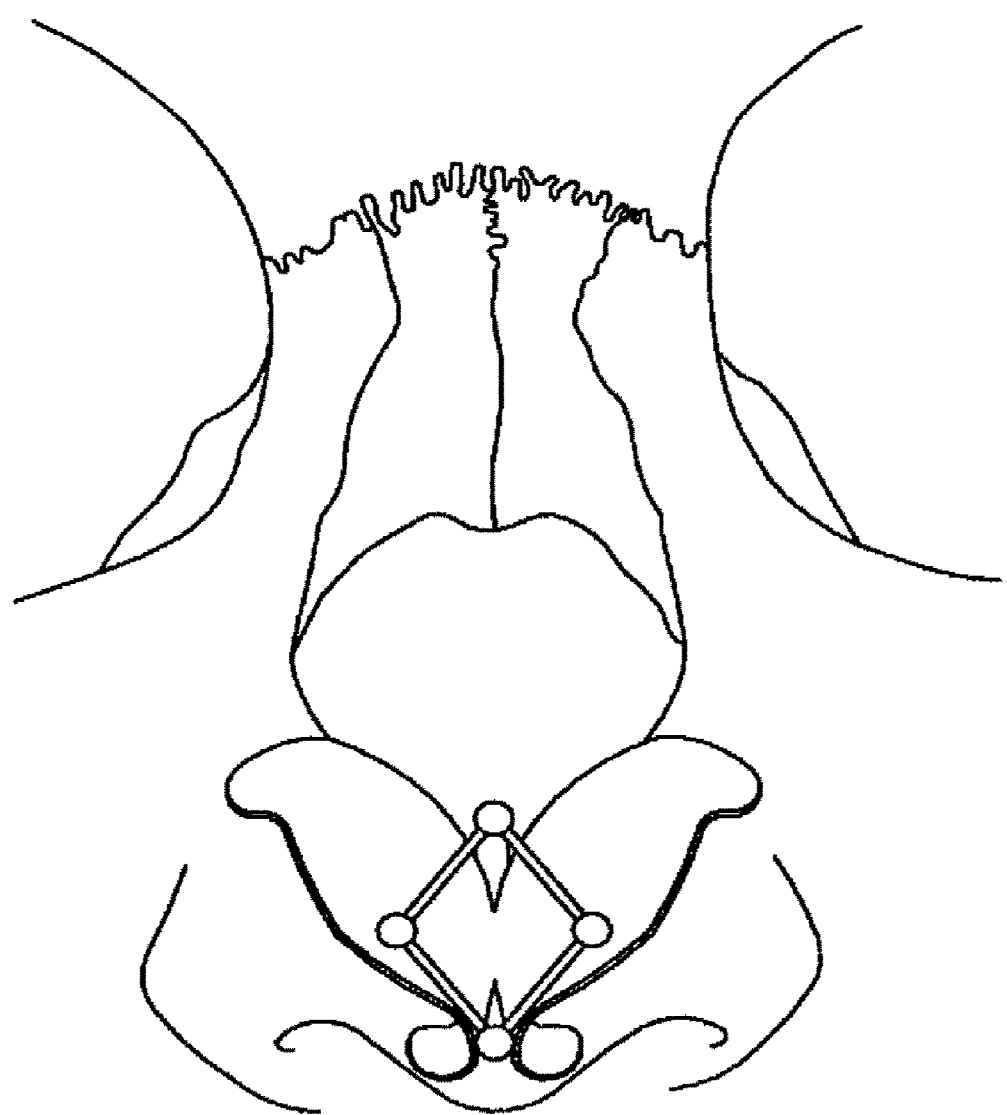
Figure 21:
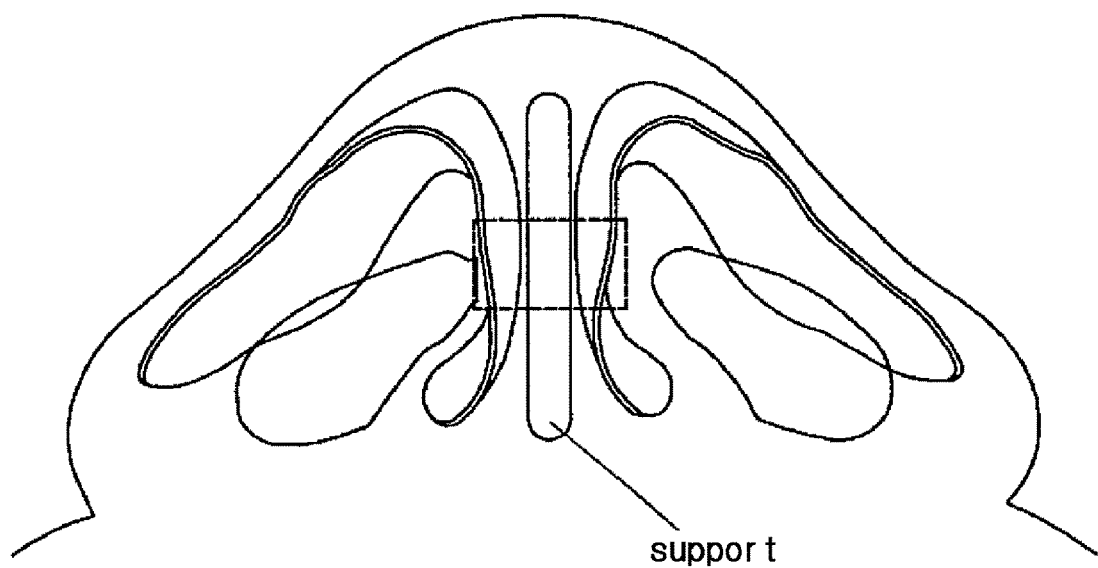
Figure 22:
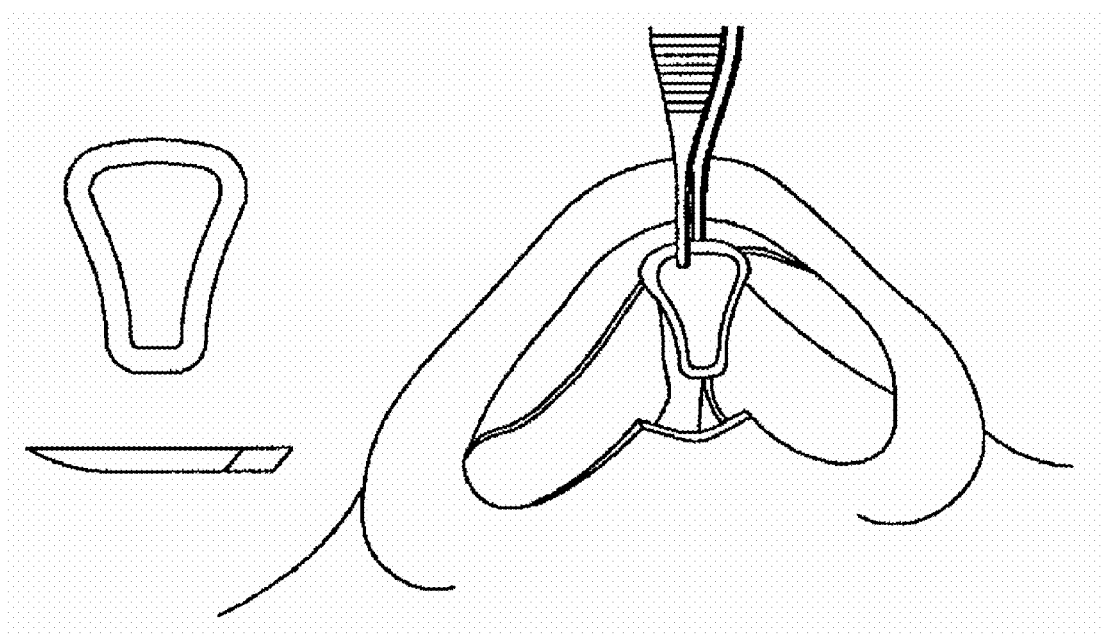
Figure 23:
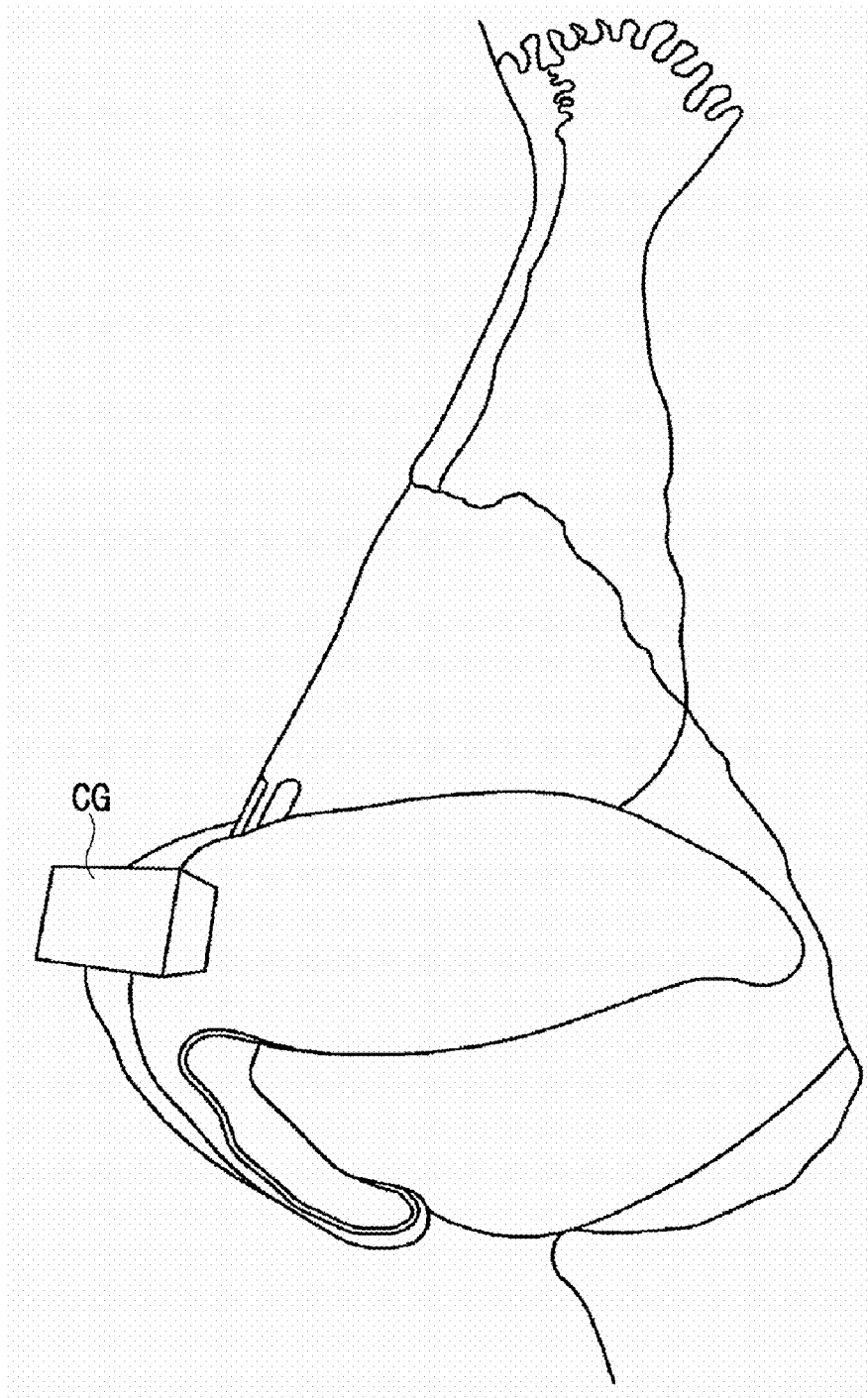
Figure 24:
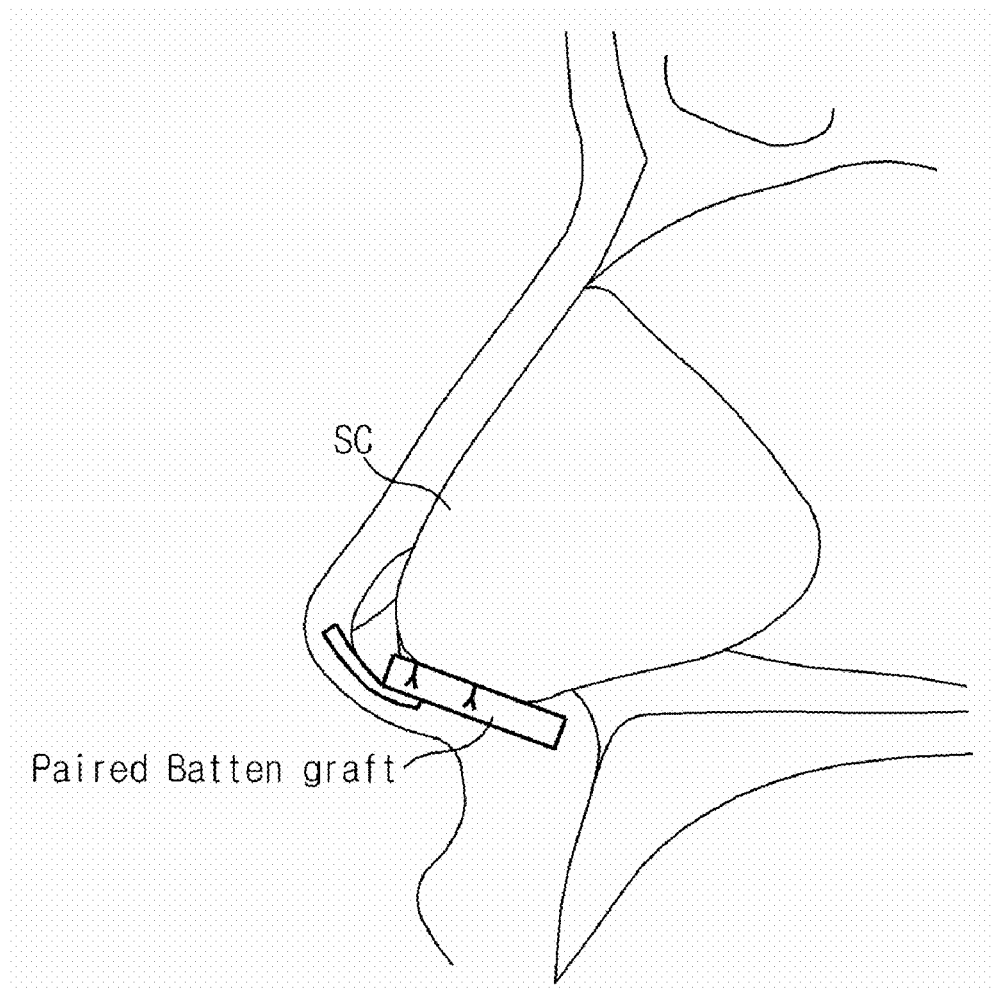
FIG. 24 is a schematic view showing surgical operation at which the paired batten graft is performed to the septal cartilage.
Figure 25:
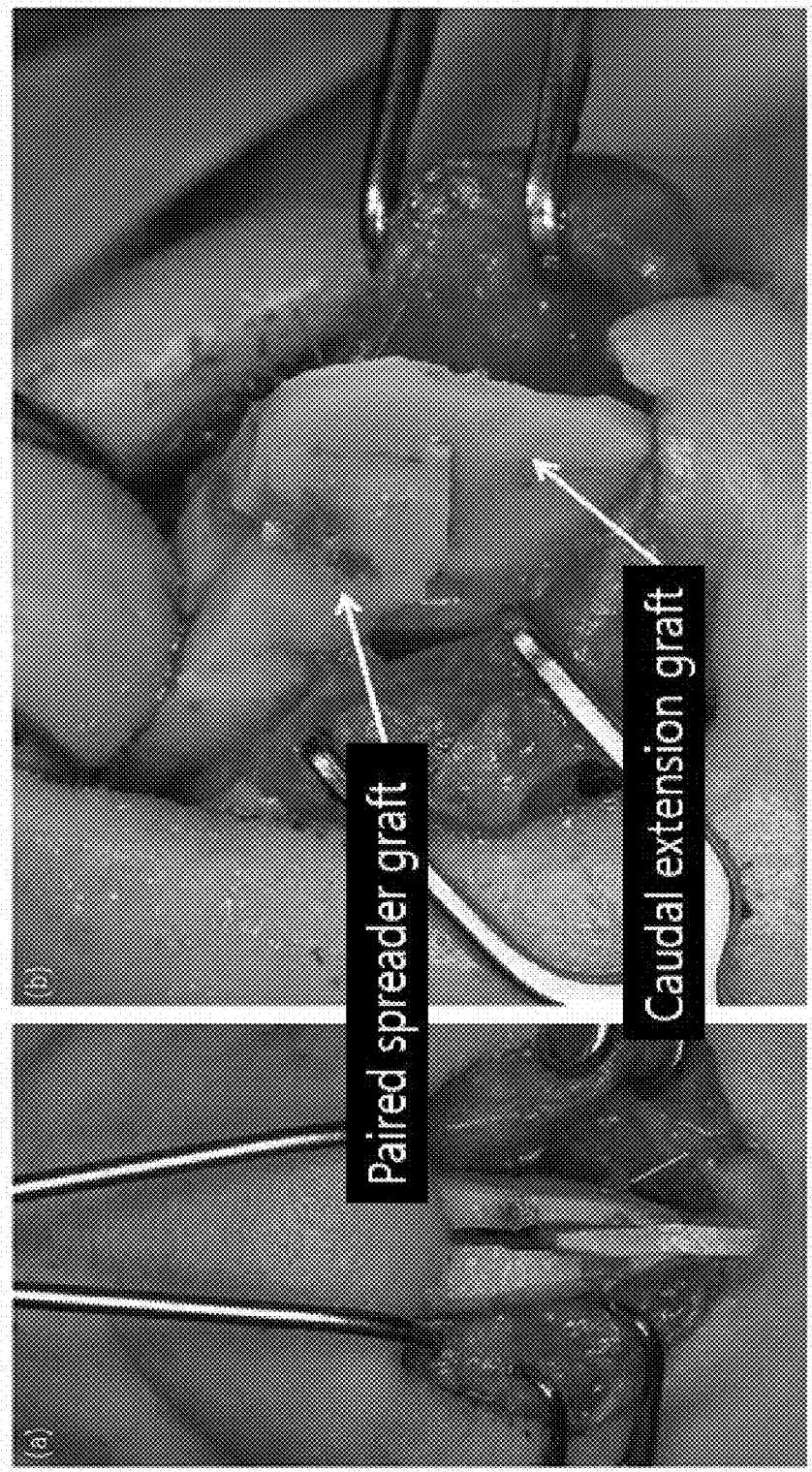
FIG. 25 is a photograph showing an actual surgical operation at which the paired spreader graft is performed to the septal cartilage.

Further, as required, onlay cap graft OCG may be secured to an upper portion of the extension graft cartilage EG to make a nasal tip into an intended shape, as shown in FIGS. 8 and 14.

Figure 26:
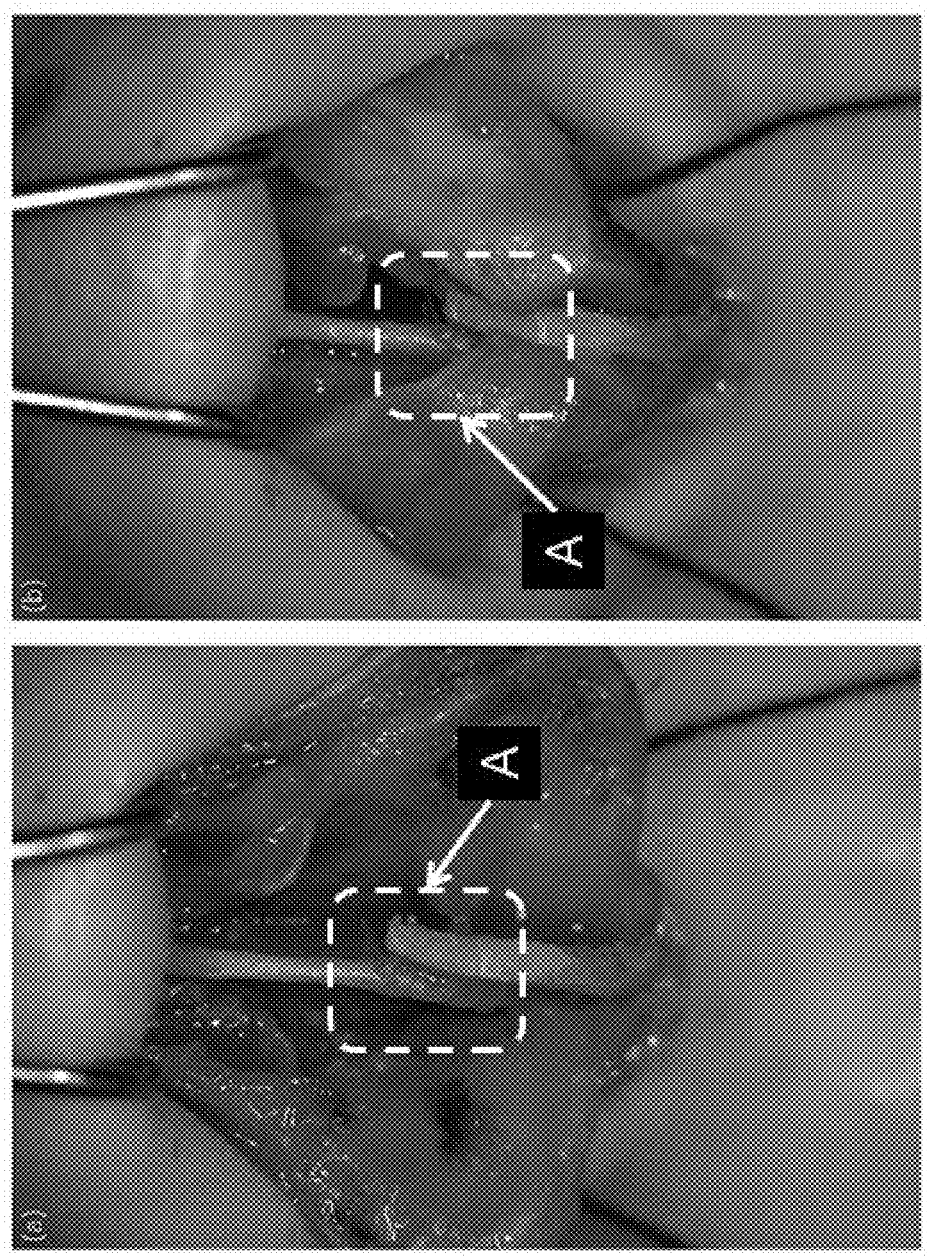
FIG. 26 is a photograph showing an actual surgical operation at which the extension graft turns its direction when the caudal septal extension graft is performed in a conventional way.

In the conventional caudal septal extension graft, the harvested and carved cartilage is doubly placed to the septal cartilage SC to perform the paired spreader graft, and then the extension graft cartilage EG is inserted between the placed cartilages. Thus, cartilage is consumed as much as the placed cartilages are used. Also, as indicated by the reference symbol A in FIG. 26, the extension graft cartilage EG may be secured in a distorted direction with respect to the nasal central direction when the extension graft cartilage EG is stitched, which may causes the nasal shape not to be accurately symmetrical after operating the nasal tip plasty.

However, if the caudal septal extension graft is operated using the aiding apparatus 60 according to the fourth embodiment of the present invention, the operation may be performed easily only with two-stage processes: namely inserting the support groove 53c of the leg part 53 into the upper border of the septal cartilage SC and securing the leg parts 53 by means of stitching sutures or push pins, and then securing the extension graft cartilage EG to the seating part 51a provided at the strut part 51 by means of stitching sutures or push pins. Thus, an amount of consumed cartilage is decreased rather than the conventional operation method, and also the possibility of side effects causing distorted nasal shape may be greatly decreased.

Fifth Embodiment

Figure 9:
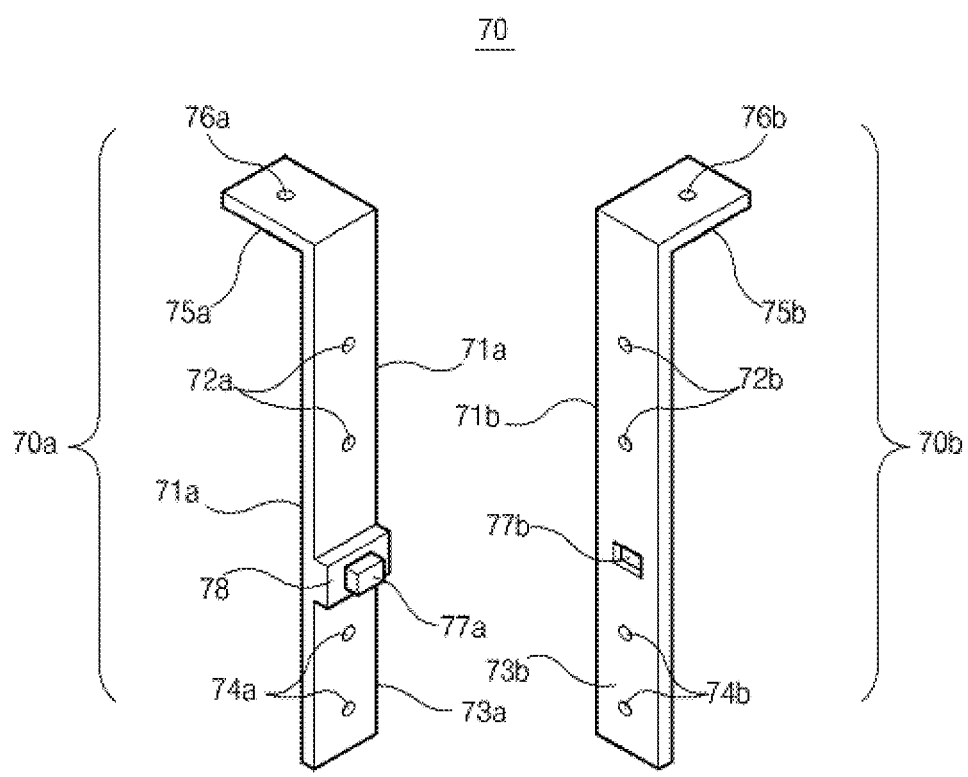
FIGS. 9 and 10 are an exploded perspective view and a front view, respectively, showing a fifth aiding apparatus for nasal tip plasty according to the fifth embodiment of the present invention.
Figure 10:
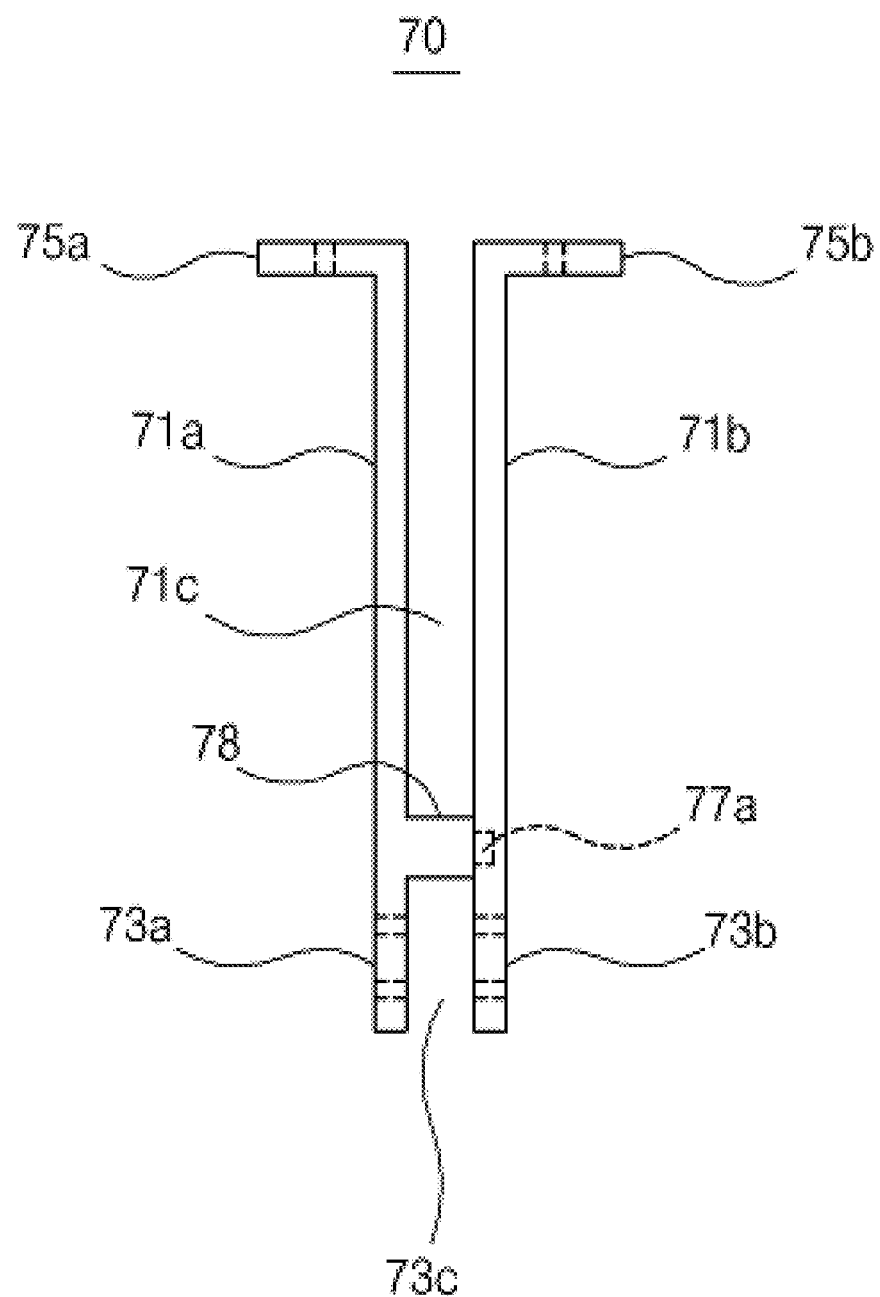

FIGS. 9 and 10 are an exploded perspective view and a front view, respectively, showing the fifth aiding apparatus for nasal tip plasty according to the fifth embodiment of the present invention.

The aiding apparatus 70 according to the fifth embodiment includes a first unit 70a and a second unit 70b which are made of a biodegradable polymer material, and coupling parts 77a and 77b which function to couple the first and second units 70a and 70b to each other.

The first unit 70a includes a first strut part 71a and a leg part 73a, and the second unit 70b includes a second strut part 71b and a leg part 73b. The coupling parts 77a and 77b comprise a first coupling unit 77a and a second coupling unit 77b.

Further, if necessary, a first ceiling part 75a and a second ceiling part 75b are provided, respectively, on the top of the first strut part 71a and the top of the second strut part 71b.

The first coupling part 77a comprises a coupling protrusion 77a, while the second coupling part 77b comprises a coupling hole 77b.

When the coupling protrusion 77a is fitted into the coupling hole 77b, a seating part 71c is provided above the coupling parts, so that cartilage strut ST is seated in the seating part. A support groove 73c is formed under the coupling parts, so that the upper border of septal cartilage SC is supported in the support groove. It would be apparent to those having ordinary skill in the art that the coupling part may be modified in various ways other than the coupling protrusion 77a and the coupling hole 77b.

The coupling protrusion 77a is provided on a base part 78. The base part 78 supports the cartilage strut ST, and defines a predetermined interval between the first and second strut parts 71a and 71b.

Further, stitching holes 72a, 74a, and 76a are formed in the first unit 70a, and stitching holes 72b, 74b, and 76b are formed in the second unit 70b. The cartilage strut ST, the cap graft cartilage CG or the septal cartilage may be stitched or connected by passing a stitching suture through the stitching holes or inserting push pins into the stitching holes.

Sixth Embodiment

Figure 11:
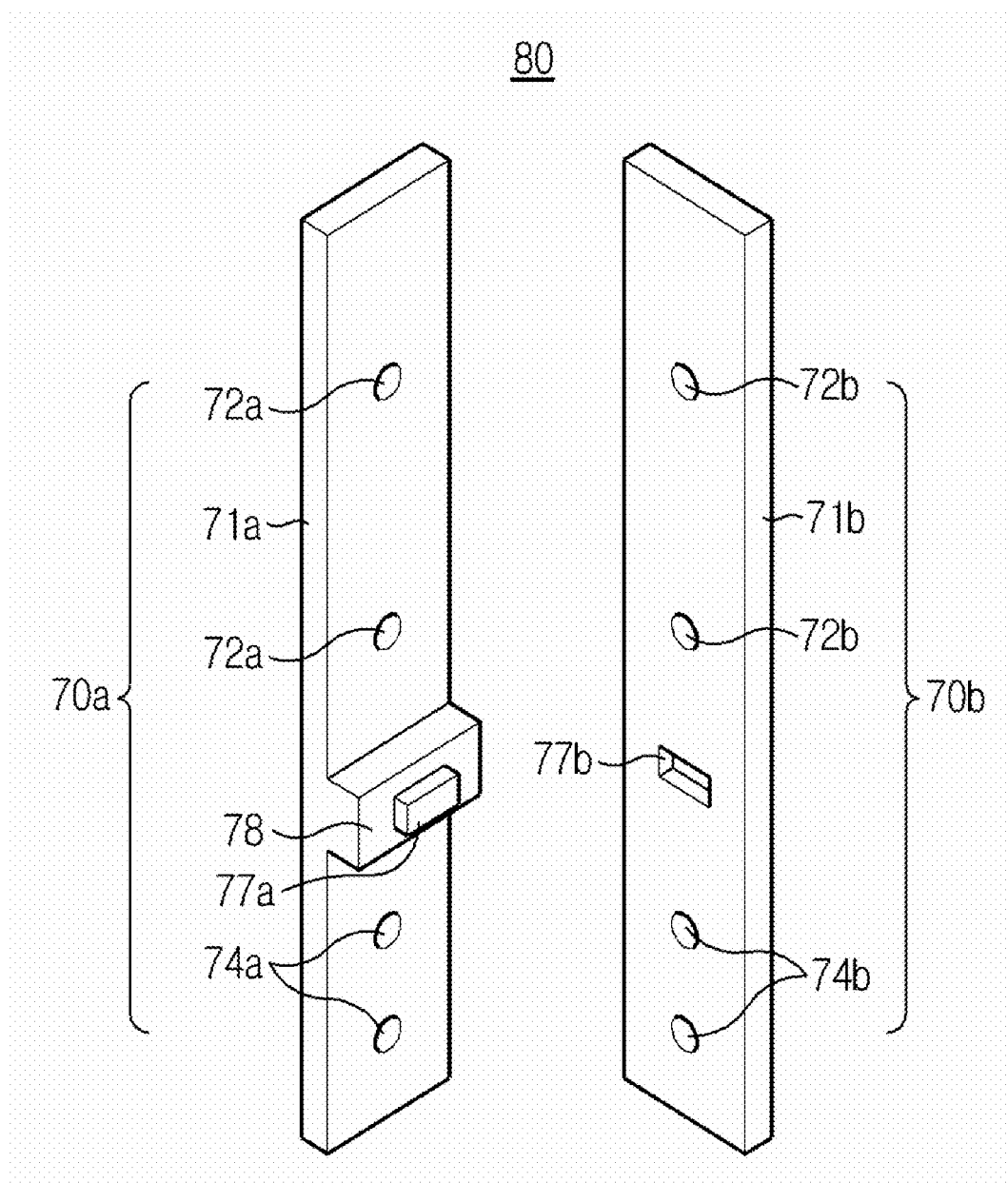
FIGS. 11 and 12 are an exploded perspective view and a front view, respectively, showing a sixth aiding apparatus for nasal tip plasty, according to the sixth embodiment of the present invention.
Figure 12:
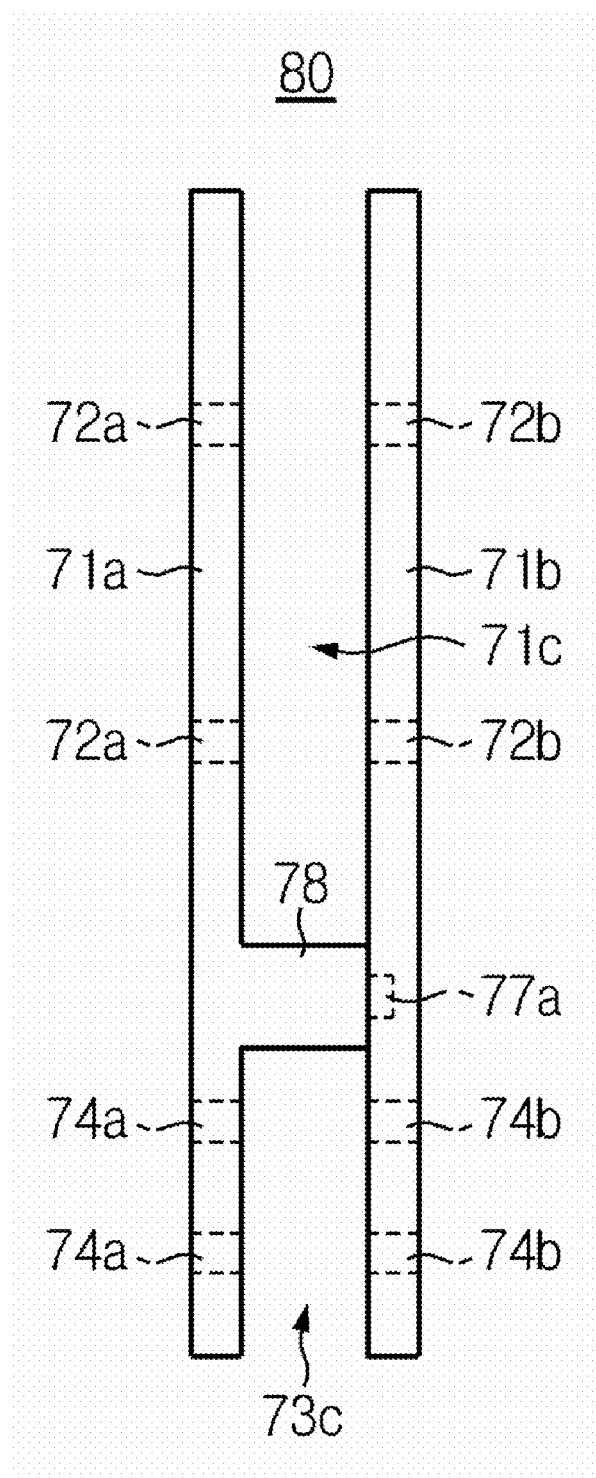

FIGS. 11 and 12 are, respectively, an exploded perspective view and a front view showing the sixth aiding apparatus for nasal tip plasty according to the sixth embodiment of the present invention.

The aiding apparatus 80 according to the sixth embodiment is substantially identical to that of the fifth embodiment, except that there is not provided the first ceiling part 75a and the second ceiling part 75b.

The aiding apparatus 80 according to the sixth embodiment may be used in the same way as that of the fourth embodiment. When the aiding apparatus 80 is used for nasal tip plasty, the coupling protrusion 77a is inserted into the coupling hole 77b to couple the first unit 70a and the second unit 70b with each other before the operation. Then, the seating part 71c is formed at the upper side of the aiding apparatus 80, and the support groove 73c is formed in the lower side thereof. The support groove 73c may be secured to the septal cartilage SC in a cephalo-caudal direction or a columellar direction of the septal cartilage, and the cartilage strut ST or the extension graft cartilage EG may be secured to the seating part 71c. If the support groove 73c is secured in a columellar direction, the cartilage strut ST may be supported. Also, if the support groove 73c is fixed in a cephalo-caudal direction, the extension graft cartilage EG may be supported.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

As described above, an aiding apparatus for nasal tip plasty according to the present invention has the following effects.

When the essential process of the nasal tip plasty is performed, that is, a cartilage strut is formed, cap grafting and shield grafting can be performed from the exterior of the operation space, thus allowing a cartilage scaffold complex to be more easily manufactured. Also, the cartilage scaffold complex may be easily held on the upper border of the septal cartilage. Thus, the present invention is advantageous in that only a minimum amount of cartilage is required, the operation period is shortened, a patient's pain is alleviated, and recovery after the operation is fast, thus allowing a beautiful nose to be more easily made.

A ceiling part is provided on the top of a strut part, so that cartilage for cap grafting can be stably held on the strut.

Further, since the strut part and the holding part are made of a degradable polymer material which is absorbable and decomposed after a predetermined period of time has passed, and a seating part is provided on the strut part so that the cartilage strut is seated on the seating part, the sensation of foreign body can be minimized.

Furthermore, the holding part includes leg parts, between which septal cartilage is inserted, and serrated parts are provided on the inner surfaces of the leg parts. Thus, the septal cartilage is secured to the holding part not by stitching using a stitching suture but by the engagement of the serrated parts, so that it is easy to apply the aiding apparatus of this invention in a narrow operation space.

In addition, if the aiding apparatus for nasal tip plasty with no ceiling part is used, there is no need to execute the paired batten graft or the paired spreader graft using autologous cartilage, which may decrease an amount of cartilage used. Also, the extension graft cartilage EG may be easily secured, which may minimize a side effect causing a distorted nasal space after the nasal tip plasty.

What is claimed is:

1. An aiding apparatus for nasal tip plasty, comprising:
a strut part extending with a column shape and having a surface to which cartilage is fixed; and
a holding part provided on a lower portion of the strut part and having a slit-type groove formed in a length direction of the strut part so that a plate-like cartilage is inserted therein, the groove being coupled to septal cartilage.

2. The aiding apparatus according to claim 1, wherein the holding part is coupled to an upper border of the septal cartilage.

3. The aiding apparatus according to claim 1, wherein the holding part is secured to an upper border of the septal cartilage in a columellar direction.

4. The aiding apparatus according to claim 2, wherein the holding part is secured to the upper border of the septal cartilage in a columellar direction.

5. The aiding apparatus according to claim 1, wherein the holding part is secured to an upper border of the septal cartilage in a cephalo-caudal direction.

6. The aiding apparatus according to claim 2, wherein the holding part is secured to the upper border of the septal cartilage in a cephalo-caudal direction.

7. The aiding apparatus according to claim 1, wherein a ceiling part is formed a top of the strut part such that cartilage for cap grafting is held thereon.

8. The aiding apparatus according to claim 1, wherein the strut part and the holding part are made of a biodegradable polymer material which is absorbed and decomposed after an elapse of a predetermined period of time.

9. The aiding apparatus according to claim 1, wherein a seating part is formed on the strut part such that cartilage strut is seated therein.

10. The aiding apparatus according to claim 1, wherein the holding part has a leg part which is coupled to the septal cartilage.

11. The aiding apparatus according to claim 10, wherein the leg part has serrated parts on inner surfaces at both sides thereof.

12. The aiding apparatus according to claim 1, wherein the strut part and the holding part comprise a first unit and a second unit, which are separative from each other, and a coupling part for coupling the first unit and the second unit with each other.

13. The aiding apparatus according to claim 12, wherein a seating part is formed at an upper side of the coupling part such that cartilage strut is inserted therein, and a leg part is formed at a lower side of the coupling part such that the leg part is inserted into the septal cartilage.

14. The aiding apparatus according to claim 1, wherein stitching holes are formed in the strut part and the holding part.

15. The aiding apparatus according to claim 7, wherein stitching holes are formed in the strut part, the holding part and the ceiling part.

* * * * *